United States Patent
Arimitsu

(10) Patent No.: US 12,404,240 B2
(45) Date of Patent: Sep. 2, 2025

(54) PHOTOBASE GENERATOR, COMPOUND, PHOTOREACTIVE COMPOSITION, AND REACTION PRODUCT

(71) Applicant: Tokyo University of Science Foundation, Tokyo (JP)

(72) Inventor: Koji Arimitsu, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 828 days.

(21) Appl. No.: 17/641,589

(22) PCT Filed: Sep. 10, 2020

(86) PCT No.: PCT/JP2020/034263
§ 371 (c)(1),
(2) Date: Mar. 9, 2022

(87) PCT Pub. No.: WO2021/049564
PCT Pub. Date: Mar. 18, 2021

(65) Prior Publication Data
US 2022/0340528 A1 Oct. 27, 2022

(30) Foreign Application Priority Data

Sep. 10, 2019 (JP) ................ 2019-164869

(51) Int. Cl.
*C07D 211/94* (2006.01)
(52) U.S. Cl.
CPC ................ *C07D 211/94* (2013.01)
(58) Field of Classification Search
CPC .................................................. C07D 211/94
USPC ........................................................ 546/192
See application file for complete search history.

(56) References Cited

FOREIGN PATENT DOCUMENTS

EP 3725815 A1 10/2020

OTHER PUBLICATIONS

Arimitsu et al. "Application to Photoreactive Materials of Photochemical Generation of Superbases with High Efficiency Based on Photodecarboxylation Reactions" Chem.Mater.2013, 25, 4461-4463.
Cameron et al. "Photogeneration of Organic Bases from o-Nitrobenzyl-Derived Carbamates" J.Am.Chem.Soc.1991, 113, 4303.

*Primary Examiner* — Kristin A Vajda
(74) *Attorney, Agent, or Firm* — Banner & Witcoff, Ltd.

(57) ABSTRACT

A photobase generator includes a compound including: first skeletons represented by the following formula (a); and a second skeleton including nitrogen atoms bonding to bonding positions of the first skeletons to form amide groups, wherein, in a molecule, a number of the first skeletons is two or more, a number of the nitrogen atoms, configuring the amide groups, in the second skeleton is the same as the number of the first skeletons, and at least one of the nitrogen atoms configuring the amide groups is converted into a nitrogen atom configuring a secondary amine or a tertiary amine by light irradiation. In the formula (a), G is a divalent aromatic group, and * represents the bonding position with the nitrogen atom.

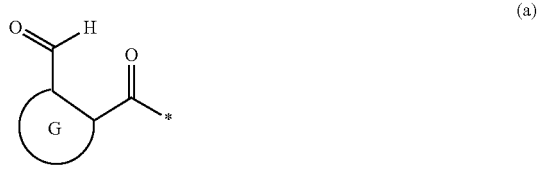

(a)

6 Claims, 10 Drawing Sheets

PHOTOBASE GENERATOR, COMPOUND, PHOTOREACTIVE COMPOSITION, AND REACTION PRODUCT

CROSS-REFERENCE TO RELATED APPLICATIONS

This application is a National Stage Application under 35 U.S.C. 371 of co-pending PCT application number PCT/JP2020/034263 designating the United States and filed Sep. 10, 2020, which claims the benefit of JP application number 2019-164869 and filed Sep. 10, 2019, each of which are hereby incorporated by reference in their entireties.

TECHNICAL FIELD

The present invention relates to a photobase generator, a compound, a photoreactive composition, and a reaction product.

BACKGROUND ART

Photopolymerizable materials to be polymerized when irradiated with light are widely practically used, and hold predominant positions in the fields of, for example, electronic materials or printing materials, because polymerization reactions thereof can be precisely controlled by relatively simple operations.

Photopolymerizable materials which have been heretofore actively studied are, for example, a radical polymerization resin composition including a photoinitiator that generates radical species by exposure, and a radical-polymerizable monomer or oligomer, and an acid catalyst-based resin composition including a photoacid generator that generates acid by exposure, and a monomer or oligomer to be polymerized by the action of an acid.

Base catalyst-based photopolymerizable materials are also known as photopolymerizable materials, such a base catalyst-based photopolymerizable material including a photobase generator that generates base by exposure, and a monomer or oligomer to be polymerized by the action of a base. A photobase generator known is, for example, an ionic photobase generator corresponding to a salt of a strong base such as guanidine and a carboxylic acid (see, for example, Non-Patent Literature 1). In such an ionic photobase generator, along with progression of a decarboxylation reaction in a carboxy group by exposure, a base is generated by elimination of the strong base forming the salt together with the carboxy group.

However, such an ionic photobase generator has a problem of being low in stability during storage and low in solubility, although high in reactivity. A resin composition using such an ionic photobase generator also has the problem of being low in stability.

On the contrary, non-ionic photobase generators have also been studied. A non-ionic photobase generator known is, for example, a non-ionic photobase generator that is a carbamate having a nitrobenzyl skeleton, in which a base is generated by not only progression of a decarboxylation reaction by exposure, but also elimination of a primary amine or secondary amine (see, for example, Non-Patent Literature 2). Such a non-ionic photobase generator allows the above problems about ionic photobase generators to be solved.

[Non-Patent Literature 1] K. Arimitsu, R. Endo, Chem. Mater. 2013, 25, 4461-4463.

[Non-Patent Literature 2] J. F. Cameron, J. M. J. Frechet, J. Am. Chem. Soc. 1991, 113, 4303.

SUMMARY OF INVENTION

Technical Problem

However, because a non-ionic photobase generator disclosed in the Non-Patent Literature 2 generate a weak base, a resin composition using it still had room for improvement in terms of improving reactivity when irradiated with light.

An object of the invention is to provide a photobase generator and a compound capable of preparing a photoreactive composition excellent in the reactivity when irradiated with light, a photoreactive composition, excellent in the reactivity when irradiated with light, and a reaction product obtained by reacting the photoreactive composition.

Solution to Problem

Specific means for solving the above problem are shown below.

<1> A photobase generator, comprising a compound including: first skeletons represented by the following formula (a); and a second skeleton including nitrogen atoms bonding to bonding positions of the first skeletons to form amide groups, wherein, in a molecule, a number of the first skeletons is two or more, a number of the nitrogen atoms, configuring the amide groups, in the second skeleton is the same as the number of the first skeletons, and at least one of the nitrogen atoms configuring the amide groups is converted into a nitrogen atom configuring a secondary amine or a tertiary amine by light irradiation.

(a)

In the formula (a), G is a divalent aromatic group, and * represents the bonding position with the nitrogen atom.

<2> The photobase generator according to <1>, wherein the second skeleton is a structure represented by the following formula (b).

(b)

(In formula (b), each $R_y$ independently represents a hydrogen atom or a hydrocarbon group that may have a substituent; * represents a bonding position that forms a single bond by bonding with * in formula (a); ** represents a bonding position bonded to $R_x$, which is an n-valent linking group, or a bonding position to a linear chain or a side chain of a high molecular compound. n represents an integer of 2 or more, and is a same value as the number of the first skeletons. Each $R_y$ may be independently bonded to $R_x$ or the linear chain or the side chain of the high molecular compound to form a ring structure. The n first skeletons bonded to * in the formula (b) may be the same or different.)

<3> The photobase generator according to <1>, wherein the number of the first skeletons is two, and the second skeleton is a structure represented by the following formula (b-1).

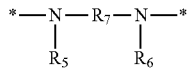
(b-1)

(In formula (b-1), each of $R_5$ and $R_6$ independently represents a hydrogen atom or a hydrocarbon group that may have a substituent; $R_7$ represents a divalent linking group; * represents a bonding position that forms a single bond by bonding with * in formula (a). Two or more of $R_5$ to $R_7$ may be independently bonded to each other to form a ring structure. The two first skeletons bonded to * in the formula (b-1) may be the same or different.)

<4> A compound comprising: first skeletons represented by the following formula (a); and a second skeleton including nitrogen atoms bonding to bonding positions of the first skeletons to form amide groups, wherein, in a molecule, a number of the first skeletons is two or more, a number of the nitrogen atoms, configuring the amide groups, in the second skeleton is the same as the number of the first skeletons, and at least one of the nitrogen atoms configuring the amide groups is converted into a nitrogen atom configuring a secondary amine or a tertiary amine by light irradiation.

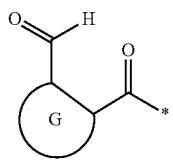
(a)

(In formula (a), G is a divalent aromatic group, and * represents the bonding position with the nitrogen atom.)

<5> The compound according to <4>, wherein the second skeleton is a structure represented by the following formula (b).

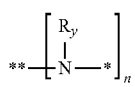
(b)

(In formula (b), each $R_y$ independently represents a hydrogen atom or a hydrocarbon group that may have a substituent; * represents a bonding position that forms a single bond by bonding with * in formula (a); ** represents a bonding position bonded to $R_x$, which is an n-valent linking group, or a bonding position to a linear chain or a side chain of a high molecular compound. n represents an integer of 2 or more, and is a same value as the number of the first skeletons. Each $R_y$ may be independently bonded to $R_x$ or the linear chain or the side chain of the high molecular compound to form a ring structure The n first skeletons bonded to * in the formula (b) may be the same or different.)

<6> The compound according to <4>, wherein the number of the first skeletons is two, and the second skeleton is a structure represented by the following formula (b-1).

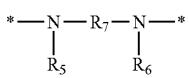
(b-1)

(In formula (b-1), each of $R_5$ and $R_6$ independently represents a hydrogen atom or a hydrocarbon group that may have a substituent; $R_7$ represents a divalent linking group; * represents a bonding position that forms a single bond by bonding with * in formula (a). Two or more of $R_5$ to $R_7$ may be independently bonded to each other to form a ring structure. The two first skeletons bonded to * in the formula (b-1) may be the same or different.)

<7> A photoreactive composition, comprising: the photobase generator according to any one of <1> to <3>; and a base-reactive compound, wherein the base-reactive compound includes a functional group that is converted, by the action of a base, into a group exhibiting reactivity, or includes a group that reacts in response to the action of a base.

<8> A reaction product obtained by reacting the photoreactive composition according to <7>.

Advantageous Effects of Invention

The invention can provide a photobase generator and a compound capable of preparing a photoreactive composition excellent in the reactivity when irradiated with light, a photoreactive composition excellent in the reactivity when irradiated with light, and a reaction product obtained by reacting the photoreactive composition.

DESCRIPTION OF EMBODIMENTS

Figure 1:
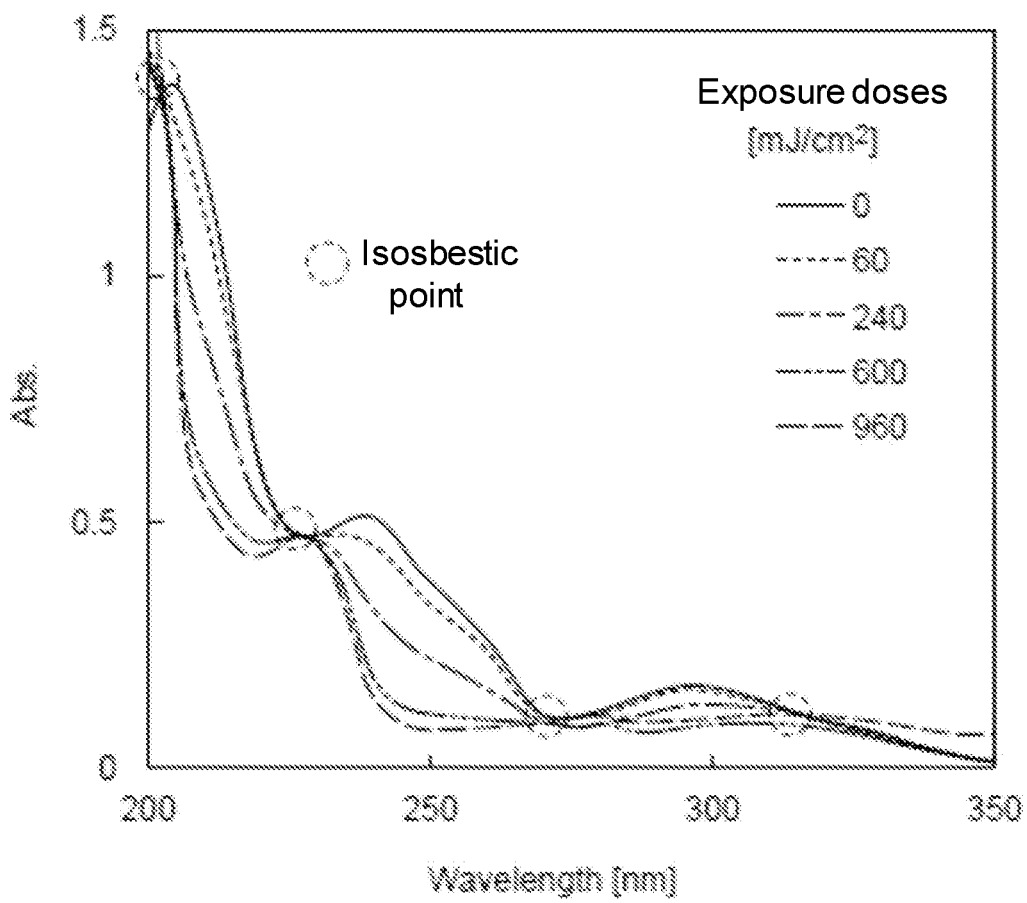
FIG. 1 is data that illustrates the measurement result of the absorbance of a compound (1)-1 in Test Example 1.

A numerical value range herein represented by "(from) . . . to . . . " means that numerical values described before and after "to" are encompassed as the lower limit and the upper limit, respectively.

[Photobase Generator]

A photobase generator in the disclosure includes a compound including: first skeletons represented by the following formula (a); and a second skeleton including nitrogen atoms bonding to bonding positions of the first skeletons to form amide groups, in which, in a molecule, a number of the first skeletons is two or more, a number of the nitrogen atoms, configuring the amide groups, in the second skeleton is the same as the number of the first skeletons, and at least one of the nitrogen atoms configuring the amide groups is converted into a nitrogen atom configuring a secondary amine or a tertiary amine by light irradiation.

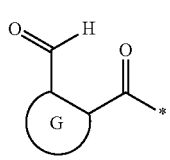

(a)

In formula (a), G is a divalent aromatic group, and * represents the bonding position with the nitrogen atom.

For example, the photobase generator in the disclosure is used for preparation of a photoreactive composition capable of producing a reaction product by light irradiation. More specifically, the base is generated from the photobase generator by irradiating the photoreactive composition including the photobase generator with light. The functional group, which is included in the base-reactive compound of the photoreactive composition, is converted by the action of the base to exhibit reactivity, or the functional group, which is included in the base-reactive compound, reacts by the action of the base. Thus, because the aforementioned photoreactive composition is irradiated with light to generate a base, the base-reactive compound included in the photoreactive composition is reacted, and the reaction product is obtained.

The photobase generator in the disclosure includes the compound (in the disclosure, also referred to as "compound (1)") including the first skeletons represented by the formula (a) and the second skeleton including nitrogen atoms bonding to the bonding positions of the first skeletons to form the amide groups, and generating the base by light irradiation. Further, in the compound (1), as shown by the following formula (i), the cyclization reaction proceeds so that formyl groups and amide groups disappear by light irradiation, and a compound (in the disclosure, also referred to as "compound (1')") represented by the following formula (1') is generated. X in the compound (1) is the second skeleton, n represents the number of the first skeletons, and is an integer of 2 or more. This compound (1') is an amine compound in which nitrogen atoms constituting amide groups of X in the compound (1) are converted into nitrogen atoms that form a secondary amine or a tertiary amine by light irradiation.

In the following formula (i), the aldehyde groups in the n first skeletons are converted into the lactone structures by light irradiation, but in the disclosure, an aldehyde group in at least one first skeleton may be converted into a lactone structure by light irradiation. From the point that the reactivity of the base-reactive compound when irradiated with light becomes better, it is preferable that the aldehyde groups in the n first skeletons are converted into the lactone structures by light irradiation, that is, the n nitrogen atoms bonding to the bonding positions of the first skeletons to form the amide groups are converted into the nitrogen atoms that form a secondary amine or a tertiary amine by light irradiation.

Herein, "secondary amine" means a base having a structure in which one hydrogen atom is directly bonded to a nitrogen atom in X bonded to a carbon atom of a carbonyl group, and "tertiary amine" means a base having a structure in which no hydrogen atom is directly bonded to a nitrogen atom in X which is bonded to a carbon atom of a carbonyl group.

The compound (1) is a non-ionic photobase generator, and unlike conventional ionic photobase generators, it has high stability during storage and high solubility, and a photoreactive composition using the compound (1) is highly stable. Further, the photoreactive composition using the photobase generator including the compound (1) has good reactivity of the base-reactive compound when irradiated with light.

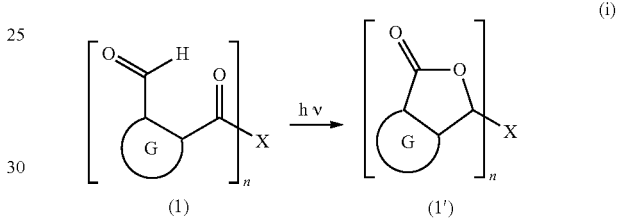

(i)

In the formula (a), G is a divalent aromatic group, and a formyl group (—C(=O)—H) and —C(=O)—* are bonding with G.

The respective bonding positions of the formyl group and —C(=O)—* to G are in an ortho-position. In other words, an atom to which the formyl group is bonding and an atom to which —C(=O)—* is bonding, among atoms included in a ring skeleton of G, are adjacent to each other in the ring skeleton of G and are directly bonding to the ring skeleton.

The aromatic group in G may be any of a divalent aromatic hydrocarbon group or a divalent aromatic heterocyclic group, or may be a divalent group (in the disclosure, such a group is regarded as an aromatic heterocyclic group) obtained by ring fusion of an aromatic hydrocarbon group and an aromatic heterocyclic group.

The aromatic hydrocarbon group and the aromatic heterocyclic group may have a substituent.

The "aromatic hydrocarbon group having a substituent" means that one or more hydrogen atoms included in the aromatic hydrocarbon group is substituted with any group (substituent) other than a hydrogen atom.

The "aromatic heterocyclic group having a substituent" means that one or more hydrogen atoms included in the aromatic heterocyclic group is substituted with any group (substituent) other than a hydrogen atom.

The aromatic group in G may be either monocyclic or polycyclic, and the number of atoms (number of ring members) included in the ring skeleton is not particularly limited, and is preferably from 3 to 20.

Examples of the aromatic hydrocarbon group as the aromatic group in G include a 1,2-phenylene group, a naphthalene-1,2-diyl group, a naphthalene-2,3-diyl group, a toluene-2,3-diyl group, a toluene-3,4-diyl group, an o-xylene-3,4-diyl group, an o-xylene-4,5-diyl group, an m-xylene-4,5-diyl group, a p-xylene-2,3-diyl group, an anthracene-1,2-diyl group, and an anthracene-2,3-diyl group. One or more hydrogen atoms in the aromatic hydrocarbon group may be each substituted with a substituent, for example, the aromatic hydrocarbon group or alkyl group exemplified. The aromatic hydrocarbon group having such a substituent preferably has 6 to 20 carbon atoms also including carbon atom(s) of the substituent.

The alkyl group (hereinafter, sometimes referred to as "substituent alkyl group") with which one or more hydrogen atoms of the aromatic hydrocarbon group exemplified are/is substituted may be any of a linear, branched, or cyclic alkyl group, and may be any of a monocyclic or polycyclic alkyl group in a case in which the alkyl group is a cyclic alkyl group. The substituent alkyl group preferably has 1 to 10 carbon atoms.

The linear or branched substituent alkyl group preferably has 1 to 10 carbon atoms, and examples include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, and a decyl group.

The cyclic substituent alkyl group preferably has 3 to 10 carbon atoms, and examples thereof include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the same as in the substituent alkyl group.

Examples of the aromatic heterocyclic group as the aromatic group in G include a group obtained by removing two hydrogen atoms each bonding to a carbon atom or a hetero atom included in the ring skeleton, from such each aromatic heterocyclic compound.

Preferable examples of the aromatic heterocyclic compound include a compound having one or more sulfur atoms as atom(s) included in the aromatic heterocyclic skeleton (sulfur-containing aromatic heterocyclic compound), a compound having one or more nitrogen atoms as atom(s) included in the aromatic heterocyclic skeleton (nitrogen-containing aromatic heterocyclic compound), a compound having one or more oxygen atoms as atom(s) included in the aromatic heterocyclic skeleton (oxygen-containing aromatic heterocyclic compound), and a compound having two hetero atoms different from each other, selected from the group consisting of a sulfur atom, a nitrogen atom, and an oxygen atom, as atoms included in the aromatic heterocyclic skeleton.

Examples of the sulfur-containing aromatic heterocyclic compound include thiophene and benzothiophene.

Examples of the nitrogen-containing aromatic heterocyclic compound include pyrrole, imidazole, pyrazole, pyridine, pyrazine, pyrimidine, pyridazine, triazine, indole, isoindole, benzimidazole, purine, indazole, quinoline, isoquinoline, quinoxaline, quinazoline, and cinnoline.

Examples of the oxygen-containing aromatic heterocyclic compound include furan, benzofuran (1-benzofuran), and isobenzofuran (2-benzofuran).

Examples of the compound having two hetero atoms different from each other, included in the aromatic heterocyclic skeleton, include oxazole, isoxazole, thiazole, benzoxazole, benzisoxazole, and benzothiazole.

As atoms included in the ring skeleton of the aromatic heterocyclic group, the atom to which a formyl group is bonding and the atom to which —C(=O)—* is bonding, among atoms included in the ring skeleton of the aromatic heterocyclic group, may be each a carbon atom or a hetero atom, and are preferably each a carbon atom.

The number of hetero atom(s) included in the ring skeleton in the aromatic heterocyclic group is preferably from 1 to 3, and more preferably 1 or 2.

In a case in which the number of hetero atom(s) included in the ring skeleton in the aromatic heterocyclic group is two or more, such hetero atoms may be all the same, may be all different, or may be only partially the same.

Examples of the substituent in the aromatic hydrocarbon group or aromatic heterocyclic group in G include the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group the aromatic hydrocarbon group, and the aromatic heterocyclic group.

The number of such substituent(s) in the aromatic hydrocarbon group or aromatic heterocyclic group in G may be only one, or two or more, and all hydrogen atoms may be each substituted with any of the substituent. The number of such substituent(s) is, for example, preferably from 1 to 4, more preferably from 1 to 3, and still more preferably 1 or 2, depending on the number of hydrogen atoms that can be substituted.

In a case in which the number of such substituents in the aromatic hydrocarbon group or aromatic heterocyclic group is two or more, such substituents may be all the same, may be all different, or may be only partially the same.

Examples of the alkoxy group as the substituent include a monovalent group obtained by bonding the substituent alkyl group to an oxygen atom, for example, a methoxy group, an ethoxy group, a n-propoxy group, an isopropoxy group, or a cyclopropoxy group.

The aryl group bonding to an oxygen atom in the aryloxy group as the substituent may be any of a monocyclic or polycyclic aryl group, and preferably has 6 to 10 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with, for example, such an aryl group or the substituent alkyl group. The aryl group having such a substituent preferably has 6 to 10 carbon atoms also including carbon atom(s) of the substituent.

Examples of the dialkylamino group as the substituent include a monovalent group obtained by substituting each of two hydrogen atoms in an amino group (—NH$_2$) with the substituent alkyl group, such as a dimethylamino group or a methylethylamino group. Such two alkyl groups bonding to a nitrogen atom in the dialkylamino group may be the same as or different from each other.

Examples of the diarylamino group as the substituent include a monovalent group obtained by substituting each of two hydrogen atoms in an amino group with the aryl group, such as a diphenylamino group or a phenyl-1-naphthylamino group. Such aryl groups bonding to a nitrogen atom in the diarylamino group may be the same as or different from each other.

Examples of the alkylarylamino group as the substituent include a monovalent group obtained by substituting one hydrogen atom of two hydrogen atoms in an amino group with the substituent alkyl group, and substituting another hydrogen atom thereof with the aryl group, such as a methylphenylamino group.

Examples of the alkylcarbonyl group as the substituent include a monovalent group obtained by bonding the substituent alkyl group to a carbonyl group (—C(=O)—), for example, a methylcarbonyl group (acetyl group).

Examples of the arylcarbonyl group as the substituent include a monovalent group obtained by bonding the aryl group to a carbonyl group, for example, a phenylcarbonyl group (benzoyl group).

Examples of the alkyloxycarbonyl group as the substituent include a monovalent group obtained by bonding the alkoxy group to a carbonyl group, for example, a methyloxycarbonyl group (methoxycarbonyl group).

Examples of the aryloxycarbonyl group as the substituent include a monovalent group obtained by bonding the aryloxy group to a carbonyl group, for example, a phenyloxycarbonyl group (phenoxycarbonyl group).

Examples of the alkylcarbonyloxy group as the substituent include a monovalent group obtained by bonding the substituent alkyl group to a carbon atom of a carbonyloxy group (—C(=O)—O—), for example, a methylcarbonyloxy group.

Examples of the arylcarbonyloxy group as the substituent include a monovalent group obtained by bonding the aryl group to a carbon atom of a carbonyloxy group, for example, a phenylcarbonyloxy group.

Examples of the alkylthio group as the substituent include a monovalent group obtained by bonding the substituent alkyl group to a sulfur atom, for example, a methylthio group, an ethylthio group, a n-propylthio group, an isopropylthio group, or a cyclopropylthio group.

Examples of the arylthio group as the substituent include a monovalent group obtained by bonding the aryl group to a sulfur atom, for example, a phenylthio group, a 1-naphthylthio group, or a 2-naphthylthio group.

Examples of the halogen atom as the substituent include a fluorine atom (—F), a chlorine atom (—Cl), a bromine atom (—Br), and an iodine atom (—I).

Examples of the haloalkyl group as the substituent include a group obtained by substituting one or more hydrogen atoms of the substituent alkyl group with halogen atom(s).

Examples of each halogen atom in the haloalkyl group include those described above, exemplified as halogen atoms serving as substituents.

The number of halogen atom(s) in the haloalkyl group is not particularly limited, and may be one, or two or more. In a case in which the number of halogen atom(s) in the haloalkyl group is two or more, such a plurality of halogen atoms may be all the same, may be all different, or may be only partially the same. The haloalkyl group may be a perhaloalkyl group in which all hydrogen atoms in the alkyl group are each substituted with a halogen atom.

The haloalkyl group is not particularly limited, and examples thereof include a chloromethyl group, a dichloromethyl group, a trichloromethyl group, and a trifluoromethyl group.

In a case in which the substituent in the aromatic hydrocarbon group or aromatic heterocyclic group in G is, for example, an electron-donating group such as an alkoxy group, an aryloxy group, a dialkylamino group, a diarylamino group, an alkylarylamino group, an alkylthio group, or an arylthio group, in the compound (1), wavelength of light necessary for generation of the base by light irradiation becomes longer (make wavelength longer). In other words, the substituent as such an electron-donating group has the advantage of enabling wavelength of light necessary for generation of the base to become longer in the compound (1).

The position of the substituent in the aromatic hydrocarbon group or aromatic heterocyclic group is not particularly limited.

G is preferably an aromatic hydrocarbon group optionally having a substituent, such a substituent is more preferably an aromatic hydrocarbon group optionally having one or more in total of one or more kinds selected from the group consisting of an alkoxy group, an aryloxy group, a dialkylamino group, a diarylamino group, an alkylarylamino group, an alkylthio group, and an arylthio group, and examples of such G include a group represented by the following formula (a)-1.

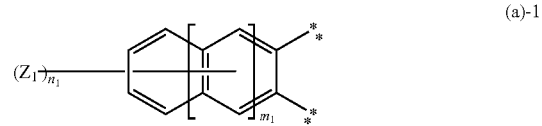

(a)-1

In the formula (a)-1, $m_1$ is an integer of 0 to 2; $n_1$ is an integer of 0 to $2m_1+4$; $Z^1$ is an alkoxy group, an aryloxy group, a dialkylamino group, a diarylamino group, an alkylarylamino group, an alkylthio group, or an arylthio group, and in a case in which $n_1$ is an integer of 2 or more, such a plurality of $Z^1$'s may be the same as or different from each other; and one bond marked with a symbol ** is formed toward a carbon atom of a formyl group, as one subject to which G is bonding, and other bond marked therewith is formed toward a carbon atom of a carbonyl group, as other subject to which G is bonding.

In the formula (a)-1, $m_1$ is an integer of 0 to 2 (0, 1, or 2), and defines the number of ring skeleton(s) included in the aromatic hydrocarbon group. In other words, the aromatic hydrocarbon group in a case in which $m_1$ is 0 is a 1,2-phenylene group, the aromatic hydrocarbon group in a case in which $m_1$ is 1 is a naphthalene-2,3-diyl group, and the aromatic hydrocarbon group in a case in which $m_1$ is 2 is an anthracene-2,3-diyl group.

In the formula (a)-1, $n_1$ is an integer of 0 to $2m_1+4$, and represents the number of bond(s) to the aromatic hydrocarbon group of $Z^1$.

In other words, in a case in which $m_1$ is 0, $n_1$ is an integer of 0 to 4, preferably an integer of 0 to 3, more preferably an integer of 0 to 2, and still more preferably 0 or 1.

In a case in which $m_1$ is 1, $n_1$ is an integer of 0 to 6, preferably an integer of 0 to 4, more preferably an integer of 0 to 3, still more preferably an integer of 0 to 2, and particularly preferably 0 or 1.

In a case in which $m_1$ is 2, $n_1$ is an integer of 0 to 8, preferably an integer of 0 to 4, more preferably an integer of 0 to 3, still more preferably an integer of 0 to 2, and particularly preferably 0 or 1.

In the formula (a)-1, $Z^1$ is an alkoxy group, an aryloxy group, a dialkylamino group, a diarylamino group, an alkylarylamino group, an alkylthio group, or an arylthio group, and is the same as in the substituent included in the aromatic hydrocarbon group or aromatic heterocyclic group in G.

In a case in which $n_1$ is an integer of 2 or more and a plurality of $Z^1$'s are present (the compound (1) has a plurality of $Z^1$'s), such a plurality of $Z^1$'s may be the same as or different from each other. In other words, such $Z^1$'s may be all the same, may be all different, or may be only partially the same.

In a case in which $n_1$ is an integer other than 0, the position of $Z^1$ bonding to the aromatic hydrocarbon group is not particularly limited.

In the formula (a)-1, one bond marked with a symbol  is formed toward a carbon atom, that is, a carbon atom of a carbonyl group in which a hydrogen atom is bonding, as one subject to which G is bonding. Other bond marked with a symbol  is formed toward a carbon atom, that is, a carbon atom of a carbonyl group adjacent to a bonding position *, as other subject to which G is bonding.

The first skeleton is preferably, for example, a group represented by the following formula (a)-2.

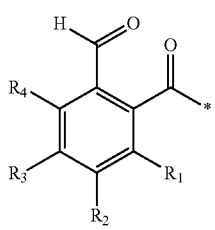

(a)-2

In the formula (a)-2, each of $R_1$ to $R_4$ independently represents a hydrogen atom, the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (halogenated alkyl group), a hydroxyl group (—OH), a mercapto group (—SH), an amino group, the aromatic hydrocarbon group, or the aromatic heterocyclic group, and * represents a bonding position with the nitrogen atom. At least two of $R_1$ to $R_4$ are optionally bonding to each other to form a ring structure.

The two or more first skeletons included in the compound (1) may be the same skeleton or different skeletons.

The second skeleton preferably has a structure represented by the following formula (b).

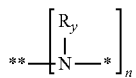

(b)

In the formula (b), each $R_y$ independently represents a hydrogen atom or a hydrocarbon group that may have a substituent, * represents a bonding position that forms a single bond by bonding with * in the formula (a), and ** represents a bonding position bonded to $R_x$, which is an n-valent linking group, or a bonding position to a linear chain or a side chain of a high molecular compound. n represents an integer of 2 or more, and is the same value as the number of the first skeletons. Each $R_y$ may be independently bonded to $R_x$ or the linear chain or the side chain of the high molecular compound to form a ring structure. The n first skeletons bonded to * in the formula (b) may be the same or different.

Examples of the n-valent linking group include an n-valent hydrocarbon group, and more specifically include an n-valent aliphatic hydrocarbon group, and an n-valent aromatic hydrocarbon group. The aliphatic hydrocarbon group may be either a saturated aliphatic hydrocarbon group or an unsaturated aliphatic hydrocarbon group.

In a case in which  is the bonding position bonded to $R_x$, which is the n-valent linking group, n is preferably 2 or 3, and more preferably 2. In a case in which  is the bonding position to a linear chain or a side chain of the high molecular compound, n is not particularly limited as long as it is two or more.

In the compound (1), it is more preferable that the number of the first skeletons is two and the second skeleton is a structure represented by the following formula (b-1).

(b-1)

In the formula (b-1), each of $R_5$ and $R_6$ independently represents a hydrogen atom or a hydrocarbon group that may have a substituent, $R_7$ represents a divalent linking group, and * represents a bonding position that forms a single bond by bonding with * in the formula (a). Two or more of $R_5$ to $R_7$ may be independently bonded to each other to form a ring structure. The two first skeletons bonded to * in the formula (b-1) may be the same or different.

Examples of the divalent linking group include a divalent hydrocarbon group, and more specifically include a divalent aliphatic hydrocarbon group, and a divalent aromatic hydrocarbon group. The aliphatic hydrocarbon group may be either a saturated aliphatic hydrocarbon group or an unsaturated aliphatic hydrocarbon group.

In the compound (1), it is still more preferable that the number of the first skeletons is two and the second skeleton is a structure represented by the following formula (b-2).

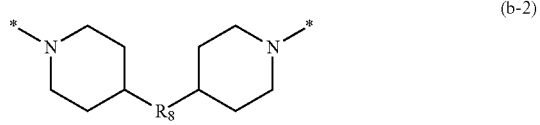

(b-2)

In the formula (b-2), $R_8$ represents a divalent linking group, * represents a bonding position that forms a single bond by bonding with * in the formula (a). The two first skeletons bonded to * in the formula (b-2) may be the same or different.

Examples of the divalent linking group include a divalent hydrocarbon group, and more specifically include a divalent aliphatic hydrocarbon group, and a divalent aromatic hydrocarbon group. The aliphatic hydrocarbon group may be either a saturated aliphatic hydrocarbon group or an unsaturated aliphatic hydrocarbon group.

The divalent hydrocarbon group is preferably a divalent linear or branched alkylene group having 1 to 20 carbon atoms, and more specifically, examples thereof include a methylene group, an ethylene group, a propanediyl group, a butanediyl group, or a pentanediyl group, a hexanediyl group, a heptanediyl group, an octanediyl group, a nonanediyl group, and a decanediyl group.

<Method of Producing Compound (1)>

For example, the compound (1) can be produced by using a method of forming an amide group.

Examples of the method for producing such a compound (1) include a producing method including a step (hereinafter, also abbreviated as "compound (1) producing step") of obtaining the compound (1) by reacting a compound (hereinafter, also abbreviated as "compound (1a)") represented by the following formula (1a) with a compound (hereinafter, also abbreviated as "compound (1b)") represented by the following formula (1b).

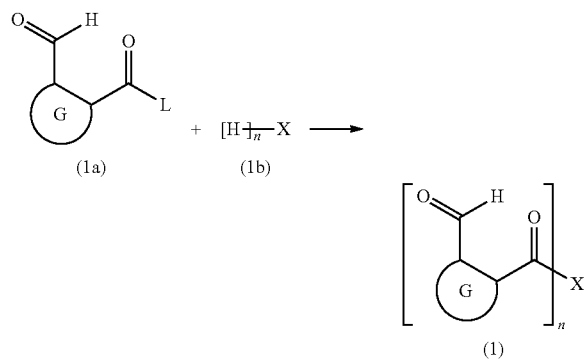

In the formula (1a), G is the same as G in the formula (a), and L is a halogen atom. In the formula (1b), X is the same as X in the compound (1). n is an integer of 2 or more.

In the formula (1a), L is a halogen atom, preferably a chlorine atom or a bromine atom, and more preferably a chlorine atom.

In the compound (1) producing step, the compound (1a) and the compound (1b) are reacted.

At the time of the reaction, the used amount of the compound (1b) with respect to the used amount of the compound (1a) may be appropriately adjusted according to the value of n. For example, in a case in which n is 2, the used amount of the compound (1b) with respect to the used amount of the compound (1a) is preferably from 0.5 times molar amount to 2.5 times molar amount and more preferably from 0.5 times molar amount to 1.8 times molar amount.

The reaction of the compound (1a) with the compound (1b) is preferably perfomed using a solvent.

The solvent is not particularly limited and may be appropriately selected depending on the types of the compound (1a) and the compound (1b). Examples of preferred solvents include ketones such as acetone; ethers such as tetrahydrofuran (THF); halogenated hydrocarbons such as dichloromethane; and amides such as N, N-dimethylformamide, and N, N-dimethylacetamide.

The solvent may be used, for example, by mixing with any component other than the solvent, such as the compound (1a) or the compound (1b) and dissolving or dispersing this component in advance, or the solvent may be used by mixing with these components without dissolving or dispersing any component other than the solvent in advance.

As the solvent, one type may be used alone, two or more types may be used in combination, and in a case in which two or more types are used in combination, the combination and ratio thereof can be arbitrarily selected.

The used amount of the solvent at the time of the reaction is not particularly limited, for example, the used amount with respect to the total used amount of the compound (1a) and the compound (1b) is preferably from 1 time by mass to 100 times by mass and more preferably from 1.5 times by mass to 60 times by mass, The temperature at the time of the reaction of the compound (1a) with the compound (1b) may be appropriately adjusted in consideration of other reaction conditions, is not particularly limited, is preferably form −5° C. to 10° C., and is more preferably from −2° C. to 5° C.

The reaction time of the compound (1a) and the compound (1b) may be appropriately adjusted in consideration of other reaction conditions, is not particularly limited, is preferably form 0.5 hours to 48 hours, and more preferably from 1 hour to 36 hours.

The reaction of the compound (1a) with the compound (1b) is preferably performed with reduced amount of water in the reaction system, for example, it is preferable to perform the reaction using a dried solvent, or to perform the reaction in an atmosphere of an inert gas such as nitrogen gas, argon gas or helium gas.

As the compound (1a), a commercially available product may be used, or a compound produced by a known method may be used.

Among the compounds (1a), those in which L is a chlorine atom are obtained by, for example, reacting a compound in which L in the formula (1a) is substituted with a hydroxyl group (—OH) (that is, a compound represented by formula "G(—CHO)—C(=O)—OH" (in the formula, G is the same as above)) with any chlorinating agent such as thionyl chloride(SOCl$_2$), sulfuryl chloride (SO$_2$Cl$_2$), phosphoryl chloride (POCl$_3$), oxalyl chloride ((COCl)$_2$), phosphorus trichloride (PCl$_3$), or phosphorus pentachloride (PCl$_5$).

In the compound (1) producing step, after completion of the reaction, the compound (1) may be taken out by performing post-treatment as necessary by a known method. That is, if necessary, the compound (1) may be taken out by performing any post-treatment operation such as filtration, washing, extraction, pH adjustment, dehydration, or concentration either alone or in combination of two or more, and then by concentration, crystallization, reprecipitation, column chromatography or the like. The compound (1) being taken out may be purified, if necessary, by performing once or more any operation such as crystallization, reprecipitation, column chromatography, extraction, or stirring and washing of crystals with a solvent, alone or in combination of two or more.

In the compound (1) producing step, after completion of the reaction, the compound (1) may be used for the intended purpose without being taken out.

In a case in which the compound (1a) obtained by producing as described above is used instead of a commercially available product, the compound (1a) is produced by the reaction, then the post-treatment may be performed as necessary in the same manner as in the case of the above compound (1), and the compound (1a) being taken out may be used in the next step, or the compound (1a) is produced by the reaction, then the post-treatment may be performed as necessary, and the reaction solution including the compound (1a) may be used in the next step without taking out the compound (1a).

Herein, the case in which the compound (1b) is reacted with the compound (1a) has been described, but for example, according to a compound in which an unintended reaction easily proceeds when reacting with the compound (1a) such as the compound (1b) having a group represented by formula "—NH—", the compound (1) may be obtained by introducing a protecting group into the corresponding group, then reacting with the compound (1a), and then performing deprotection after this reaction. As described above, the compound (1) can be easily produced by adding or changing a part of the steps in the above-mentioned producing method.

Herein, the case in which the compound (1b) is reacted with the compound (1a) has been described, but depending on the type of the objective substance, a compound represented by the following formula (1c) (hereinafter, also abbreviated as "compound (1c)") may be reacted instead of the compound (1a). In this case, the compound (1) can be produced by the same method as the above-mentioned producing method except that the compound (1c) is used instead of the compound (1a).

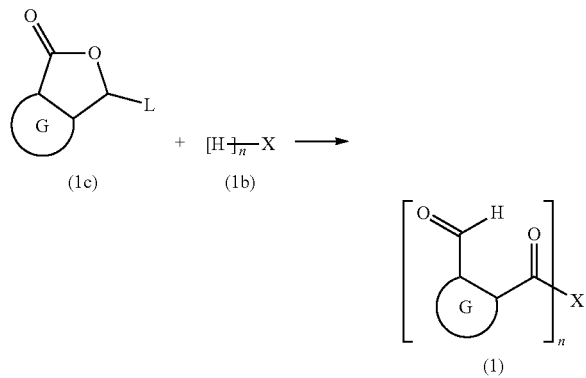

In the formula (1b) and the formula (1c), G, X, L and n are the same as described above.

Herein, as a method of producing the compound (1), the above-mentioned compound (1) producing step has been described, but the compound (1) may be produced by forming a different bond by using a combination of raw material compounds other than the compound (1a) and the compound (1b) instead of the method of forming the amide groups.

The structure of the compound (1) can be confirmed by a known method such as nuclear magnetic resonance (NMR) spectroscopy, mass spectrometry (MS), or infrared spectroscopy (IR).

[Photoreactive Composition]

The photoreactive composition in the disclosure includes the photobase generator in the disclosure, and the base-reactive compound, in which the base-reactive compound includes a functional group that is converted, by the action of a base, into a group exhibiting reactivity, or includes a group that reacts in response to the action of a base. The compound including the functional group that is converted, by the action of the base, into the group exhibiting reactivity may be a compound including only one functional group described above, may be a compound including two or more functional groups described above, or may be a mixture thereof. The compound including the group that reacts in response to the action of the base may be a compound including only one group that reacts in response to the action of the base, may be a compound including two or more groups that reacts in response to the action of the base, or may be a mixture thereof.

For example, when the photoreactive composition in the disclosure is irradiated with light, a base is generated from the photobase generator, and the functional group, which is included in the base-reactive compound of the photoreactive composition, is converted by the action of the base to exhibit reactivity, or the functional group, which is included in the base-reactive compound, reacts by the action of the base. Thus, the aforementioned photoreactive composition is irradiated with light to generate the base, thereby allowing the base-reactive compound included in the photoreactive composition to be reacted, and the reaction product is obtained.

The photoreactive composition may be a photocurable composition that is to be cured by a reaction of the base-reactive compound by light irradiation, and such a photocurable composition may be used for production of a cured product by light irradiation.

The photoreactive composition may be a photoreactive material (positive type) to be solubilized by light irradiation, or may be a photoreactive material (negative type) to be cured by light irradiation.

The photobase generator which the photoreactive composition in the disclosure includes, may be adopted singly, or in combination of two or more kinds thereof, and in a case of two or more kinds, the combination and the ratio can be arbitrarily set.

According to the photoreactive composition in the disclosure, the content ratio of the photo base generator is preferably from 4% by mass to 39% by mass, more preferably from 6% by mass to 36% by mass, still more preferably from 8% to 33% by mass, with respect to the content ratio of the base-reactive compound. When the content ratio of the photobase generator is 4% by mass or more, the reaction of the base-reactive compound proceeds more easily. When the content of the photobase generator is 39% by mass or less, overuse of the photobase generator is prevented.

(Base-Reactive Compound)

The photoreactive compound in the disclosure includes the base-reactive compound. The base-reactive compound is the compound (in the disclosure, also referred to as "base-reactive compound (9-2a)") including the functional group that is converted, by the action of the base, into the group exhibiting reactivity, or a compound (in the disclosure, also referred to as "base-reactive compound (9-2b)") including the group that reacts in response to the action of the base. The base-reactive compound (9-2b) differs from the base-reactive compound (9-2a) in that the group that reacts is not converted into a group exhibiting reactivity by the action of the base.

Examples of a reaction that proceeds in the base-reactive compound include addition polymerization and condensation polymerization.

For example, the base-reactive compound may be any of a monomer, an oligomer, and a polymer, or may be either of a low molecular compound or a high molecular compound.

As the base-reactive compound, the known compound can be used, and for example, the base-reactive compounds described in "Japanese Patent Application Laid-Open (JP-A) No. 2011-80032" can be used. However, these compounds are just an example.

Examples of the base-reactive compound (9-2a) include a compound in which the functional group is decomposed by the action of the base and converted into a group exhibiting reactivity. Examples of such a base-reactive compound (9-2a) include a compound including a carbonate skeleton (—O—C(=O)—O—), and a photosensitive polyimide.

Examples of the base-reactive compound (9-2b) include an epoxy resin, a (meth)acrylate resin, a silicon resin, and an alkoxysilane compound.

In the disclosure, "(meth)acrylate" is a concept that includes both "acrylate" and "methacrylate".

The base-reactive compound which the photoreactive composition in the disclosure includes, may be adopted singly, or in combination of two or more kinds thereof, and in a case of two or more kinds, the combination and the ratio can be arbitrarily set.

(Other Component)

The photoreactive composition in the disclosure may further include any component other than the base-reactive compound, and the photobase generator.

Such other component is not particularly limited and can be arbitrarily selected for any purpose, as long as the effect of the invention is not impaired.

Such other component included in the photoreactive composition may be adopted singly, or in combination of two or more kinds thereof, and in a case of two or more kinds, the combination and the ratio can be arbitrarily set.

Examples of such other component include sensitizers, fillers, pigments, and solvents.

<Sensitizer>

The photoreactive composition in the disclosure may include a sensitizer.

The sensitizer is not particularly limited and examples thereof include benzophenone, naphthoquinone, anthraquinone, xanthene, thioxanthene, xanthone, thioxanthone, anthracene, phenanthrene, phenanthroline, pyrene, pentacene, and derivatives thereof. Among them, for example, from the point of being excellent in photoresponsiveness of the photobase generator in the long wavelength ultraviolet region of 300 nm or more, more specifically, being excellent in photoresponsiveness to i-ray (365 nm) or longer wavelength active energy rays, and being applicable to the wider range, anthraquinone, thioxanthone, anthracene, and derivatives thereof are preferable, and thioxanthone, anthracene, and derivatives thereof are more preferable.

The sensitizer may be adopted singly, or in combination of two or more kinds thereof, and in a case of two or more kinds, the combination and the ratio can be arbitrarily set.

It is preferable that the sensitizer is at least one selected from the group consisting of a compound represented by the following formula (A), a compound represented by the following formula (B) and a compound represented by the following formula (C).

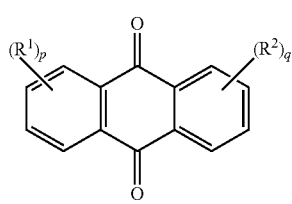

(A)

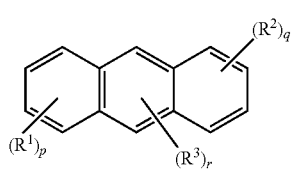

(B)

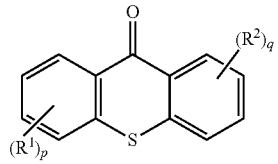

(C)

In the formulae (A) to (C), each of $R^1$, $R^2$ and $R^3$ is independently an alkyl group, an alkoxy group, an amino group, an alkylthio group, a cyano group, a halogen atom, a nitro group, a haloalkyl group, a hydroxyl group or a mercapto group, and each of p and q is independently an integer of 0 to 4, and r is an integer of 0 to 2.

In the formula (A), each of $R^1$ and $R^2$ is independently, preferably a halogen atom or an alkyl group, more preferably a halogen atom, and still more preferably a chlorine atom.

In the formula (A), each of p and q is independently, preferably an integer of 0 to 2, and more preferably 1 or 2.

In the formula (B), each of R', $R^2$ and $R^3$ is independently, preferably an alkyl group, more preferably an alkyl group having 1 to 10 carbon atoms, still more preferably an alkyl group having 1 to 5 carbon atoms, particularly preferably an alkyl group having 3 to 5 carbon atoms, and extremely preferably a branched alkyl group having 3 to 5 carbon atoms such as t-butyl group.

In the formula (B), each of p and q is independently, preferably an integer of 0 to 2, and more preferably 0 or 1. r is preferably 0 or 1, and more preferably 0.

In the formula (C), each of $R^1$ and $R^2$ is independently, preferably a halogen atom or an alkyl group.

In the formula (C), each of p and q is independently, preferably an integer of 0 to 2, and more preferably 0 or 1.

In the photoreactive composition in the disclosure, the content of the sensitizer is preferably from 30 mol % to 200 mol %, and more preferably from 50 mol % to 150 mol %, with respect to the photobase generator. When the content of the sensitizer is 30 mol % or more, a base is easily generated from the photobase generator. When the content of the sensitizer is 200 mol % or less, overuse of the sensitizer is prevented.

<Filler>

The photoreactive composition in the disclosure may include a filler. A filler can be included, thereby allowing characteristics, for example, the viscosity of the photoreactive composition itself, and the strength of the photoreactive composition (reaction product described below) after the reaction to be modulated.

The filler may be any known filler and is not particularly limited. For example, the filler may be any of a fibrous, plate-like, or granular filler, and the shape, the size, and the material thereof may be each appropriately selected for any purpose.

The filler included in the photoreactive composition may be adopted singly, or in combination of two or more kinds thereof, and in a case of two or more kinds, the combination and the ratio can be arbitrarily set.

The content of the filler in the photoreactive composition is not particularly limited and may be appropriately modulated for any purpose.

<Pigment>

The photoreactive composition in the disclosure may include a pigment. A pigment can be included, thereby allowing, for example, light permeability to be modulated.

The pigment included in the photoreactive composition may be any known pigment such as a white, blue, red, yellow, or green pigment, and is not particularly limited.

The pigment included in the photoreactive composition may be adopted singly, or in combination of two or more kinds thereof, and in a case of two or more kinds, the combination and the ratio can be arbitrarily set.

The content of the pigment in the photoreactive composition is not particularly limited and may be appropriately modulated for any purpose.

<Solvent>

The photoreactive composition in the disclosure may include a solvent. A solvent can be included, thereby allowing handleability to be enhanced.

The solvent is not particularly limited, and may be appropriately selected in consideration of solubility, stability, and the like of the base-reactive compound and the photobase generator.

The solvent is not particularly limited, and examples thereof include halogenated hydrocarbon such as dichloromethane or chloroform; aromatic hydrocarbon such as toluene, o-xylene, m-xylene, or p-xylene; aliphatic hydrocarbon such as hexane, heptane, or octane; carboxylate ester such as ethyl acetate or butyl acetate; ether such as diethyl ether, tetrahydrofuran (THF), or 1,2-dimethoxyethane (dimethylcellosolve); ketone such as acetone, methyl ethyl ketone (MEK), cyclohexanone, or cyclopentanone; nitrile such as acetonitrile; and amide such as N,N-dimethylformamide (DMF) or N,N-dimethylacetamide.

The solvent included in the photoreactive composition may be adopted singly, or in combination of two or more kinds thereof, and in a case of two or more kinds, the combination and the ratio can be arbitrarily set.

The content of the solvent in the photoreactive composition is preferably from 3 times by mass to 20 times by mass, more preferably from 4 times by mass to 15 times by mass, and still more preferably from 5 times by mass to 10 times by mass with respect to the content of the base-reactive compound. The content of the solvent is in such a range, thereby allowing the photoreactive composition to be more enhanced in handleability.

The photoreactive composition is obtained by blending the base-reactive compound, the photobase generator, and, if necessary, any other component. One obtained after blending of such respective components may be adopted as the photoreactive composition as it is, or may be, if necessary, subsequently subjected to, for example, a known purification operation, thereby obtaining the photoreactive composition.

The blending of such respective components may be performed by adding all the components and then mixing them, performing mixing while sequentially adding some of the components, or performing mixing while sequentially adding all the components.

The mixing method is not particularly limited, and may be appropriately selected from known methods including a method involving mixing under rotation of, for example, a stirring bar or a stirring blade; a method involving mixing by use of, for example, a mixer; and a method involving mixing by addition of ultrasonic wave.

The temperature in the blending is not particularly limited as long as the respective components blended are not degraded, and the temperature can be, for example, from 3° C. to 30° C.

The blending time is also not particularly limited as long as the respective components blended are not degraded, and the time can be, for example, from 30 seconds to 1 hour.

It is noted that these blending conditions are merely examples.

<Reaction Product>

The reaction product in the disclosure is obtained by reacting the photoreactive composition. The method of producing the reaction product in the disclosure is described in the section of the method of producing a reaction product in the disclosure, described below.

The shape of the reaction product in the disclosure is, for example, a film or a rod shape, and can be arbitrarily selected for any purpose.

(Method of Producing Reaction Product)

The method of producing a reaction product in the disclosure includes a step of irradiating the photoreactive composition with light, thereby generating a base from the photobase generator. In the base-reactive compound included in the photoreactive composition, the functional group included in the base-reactive compound is converted by the action of the base to exhibit reactivity, or the functional group, which is included in the base-reactive compound, reacts by the action of the base generated. Thus, because the aforementioned photoreactive composition is irradiated with light to generate the base, the base-reactive compound included in the photoreactive composition is reacted, and the reaction product is obtained.

The photoreactive composition may be attached to an objective substance according to a known procedure, and then, if necessary, pre-baked (dried), thereby forming a photoreactive composition layer, and the photoreactive composition layer may be irradiated with light.

For example, in a case in which a film-like reaction product is produced, the reaction product may be produced by coating an objective substance with the photoreactive composition by use of any of various coaters such as a spin coater, an air knife coater, a blade coater, a bar coater, a gravure coater, a roll coater, a roll knife coater, a curtain coater, a die coater, a knife coater, a screen coater, a meyer bar coater, and a kiss coater, or a coating unit such as an applicator, or dipping an objective substance in the photoreactive composition, thereby allowing the photoreactive composition to be attached to the objective substance.

For example, in a case in which a film-like or rod-like reaction product is produced, the reaction product may be produced by allowing the photoreactive composition to be attached to an objective substance by use of a printing procedure such as a screen printing method, a flexographic printing method, an offset printing method, an inkjet printing method, a dispenser printing method, a jet dispenser printing method, a gravure printing method, a gravure offset printing method, or a pad printing method.

The pre-baking may be performed in conditions of, for example, from 40° C. to 120° C. and from 30 seconds to 10 minutes, and is not particularly limited.

The wavelength of light with which the photoreactive composition is irradiated is not particularly limited, and may be, for example, any wavelength in the ultraviolet to visible region. The wavelength of light with which the photoreactive composition is irradiated may be 10 nm or more, may be 200 nm or more, or may be 300 nm or more. The wavelength of light with which the photoreactive composition is irradiated may be 600 nm or less, may be 500 nm or less, or may be 400 nm or less.

The illuminance of light with which the photoreactive composition is irradiated is, for example, preferably from 1 mW/cm$^2$ to 10 mW/cm$^2$, more preferably from 1 mW/cm$^2$ to 5 mW/cm$^2$, and still more preferably from 1 mW/cm$^2$ to 3 mW/cm$^2$.

The exposure doses with which the photoreactive composition is irradiated is, for example, preferably from 100 mJ/cm² to 10000 mJ/cm², more preferably from 200 mJ/cm² to 5000 mJ/cm², and still more preferably from 300 mJ/cm² to 3000 mJ/cm².

It is noted that light irradiation conditions here listed are merely examples and are not limited thereto.

Such a reaction product obtained by irradiating the photoreactive composition with light may be further subjected to post-baking (heating treatment after light irradiation).

The post-baking may be performed in conditions of, for example, from 80° C. to 180° C. and from 20 minutes to 2 hours, and is not particularly limited.

The thickness of the reaction product may be appropriately set for any purpose, and is not particularly limited. The thickness of the reaction product is, for example, preferably from 1 μm to 500 μm and more preferably from 5 μm to 200 μm. A reaction product having such a thickness can be formed by, for example, setting the thickness of the photoreactive composition layer to any thickness equal to or more than the thickness of an objective reaction product.

For example, the ratio of the thickness of the reaction product (thickness of photoreactive composition layer after light irradiation) with respect to the thickness of the photoreactive composition layer (thickness of photoreactive composition layer before light irradiation) ([thickness of photoreactive composition layer after light irradiation]/[thickness of photoreactive composition layer before light irradiation]) can be, for example, from 0.2 to 1.0, and can be any of from 0.3 to 1.0, from 0.4 to 1.0, from 0.5 to 1.0, from 0.6 to 1.0, from 0.7 to 1.0, from 0.8 to 1.0, or from 0.9 to 1.0, by further modulation of reaction conditions.

EXAMPLES

Hereinafter, the invention will be more specifically described with reference to Examples, but the invention is not limited by these Examples.

<Production of compound (1)-1>

As shown below, 3-bromophthalide was reacted with 4,4'-trimethylenedipiperidine to produce a compound (1)-1.

In practice, a mixture of 4,4'-trimethylenedipiperidine (1.1 g, 0.011 mol) and dried dichloromethane (40 mL) was added to a liquid mixture of 3-bromophthalide (2.1 g, 0.010 mol), dried dichloromethane (40 mL) and triethyleneamine (2.4 g, 0.022 mol), and the thus-obtained liquid mixture was stirred at 0° C. for 14 hours to perform the reaction. After completion of the reaction, unreacted 4,4'-trimethylene dipiperidine was distilled off under reduced pressure from the reaction solution.

Next, dichloromethane was added to the obtained reaction solution, hydrochloric acid having a concentration of 5% by mass was further added thereto, and then the reaction solution was washed by shaking in a separating funnel. The washing with this hydrochloric acid was performed once more, and a total of twice.

Next, a saturated aqueous sodium hydrogen carbonate solution was added to the reaction solution after washing with the hydrochloric acid, and then the reaction solution was washed by shaking in a separating funnel. The washing with this saturated aqueous sodium hydrogen carbonate solution was performed once more, and a total of twice.

Next, a saturated aqueous sodium chloride solution was added to the reaction solution after washing with the saturated aqueous sodium hydrogen carbonate solution, and then the reaction solution was washed by shaking in a separating funnel. The washing with this saturated aqueous sodium chloride solution was performed once more, and a total of twice.

Next, the reaction solution after washing with the saturated aqueous sodium chloride solution was purified by silica gel column chromatography using ethyl acetate as the mobile phase, and the objective compound (1)-1 was obtained as a white solid (yield 53%).

Regarding the obtained compound (1)-1, the analysis result of ¹H-NMR is shown in Table 1.

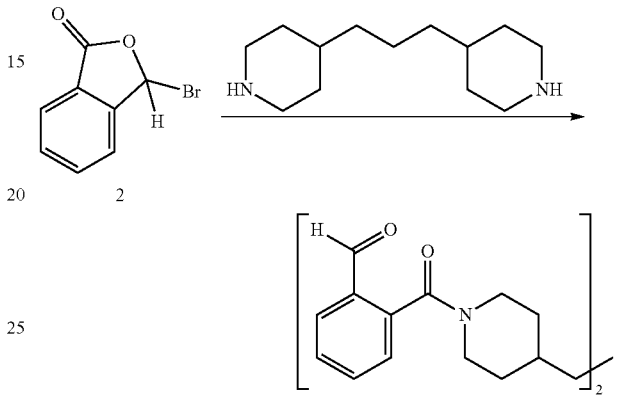

TABLE 1

| ¹H-NMR [δ/ppm] (CHCl₃, 300 MHz) | 0.99 (t, 1H, J = 6.0 Hz, —CH₂—CH₂—CH₂—) |
|---|---|
| | 1.24 (m, 2H, —N(CH₂)₂—(CH₂)₂—) |
| | 1.50 (br, 2H, —CH—CH₂—CH₂—) |
| | 1.80 (m, 1H, —CH—) |
| | 2.77 (dt, 1H, J = 6.0, 21 Hz, —N(CH₂)₂—) |
| | 2.91 (dt, 2H, J = 6.0, 21 Hz, —N(CH₂)₂—) |
| | 3.32 (dt, 1H, J = 6.0, 21 Hz, —N(CH₂)₂—) |
| | 4.76 (dt, 1H, J = 6.0, 21 Hz, —N(CH₂)₂—) |
| | 7.3-7.9 (m, 4H, Ar—H) |
| | 10.0 (s, 1H, CHO) |

<Production of Compound (2)-1>

As shown below, a reaction product of phthalaldehyde acid and thionyl chloride was reacted with piperidine to produce a compound (2)-1.

In practice, phthalaldehyde acid (8.04 g, 53.6 mmol) was added to thionyl chloride (32.0 g, 269 mmol), dried DMF (4 mL) was further added thereto, and the thus-obtained mixture was stirred at room temperature for 3 hours to perform the reaction. After completion of the reaction, unreacted thionyl chloride was distilled off under reduced pressure from the reaction solution.

Separately, dried THF (20 mL) was added to piperidine (13.0 g, 152 mmol), and the reaction solution after distilling off thionyl chloride under reduced pressure was further added thereto, and the thus-obtained mixture was stirred at 0° C. for 4 hours to perform the reaction. After completion of the reaction, the solvent was distilled off.

Next, dichloromethane was added to the obtained reaction solution, hydrochloric acid having a concentration of 5% by mass was further added thereto, and then the reaction solution was washed by shaking in a separating funnel. The washing with this hydrochloric acid was performed once more, and a total of twice.

Next, a saturated aqueous sodium hydrogen carbonate solution was added to the reaction solution after washing with the hydrochloric acid, and then the reaction solution was washed by shaking in a separating funnel. The washing with this saturated aqueous sodium hydrogen carbonate solution was performed once more, and a total of twice.

Next, a saturated aqueous sodium chloride solution was added to the reaction solution after washing with the saturated aqueous sodium hydrogen carbonate solution, and then the reaction solution was washed by shaking in a separating funnel. The washing with this saturated aqueous sodium chloride solution was performed once more, and a total of twice.

Next, the reaction solution after washing with the saturated aqueous sodium chloride solution was purified by silica gel column chromatography using a mixed solvent of ethyl acetate/n-hexane (1/1, volume ratio) as the mobile phase, and by collecting and concentrating the fractions including the objective substance, the objective compound (2)-1 was obtained as a yellow viscous liquid (yield 11.4 g, yield 98%).

Regarding the obtained compound (2)-1, the analysis results of $^1$H-NMR, $^{13}$C-NMR, and ESI-MS are shown in Table 2.

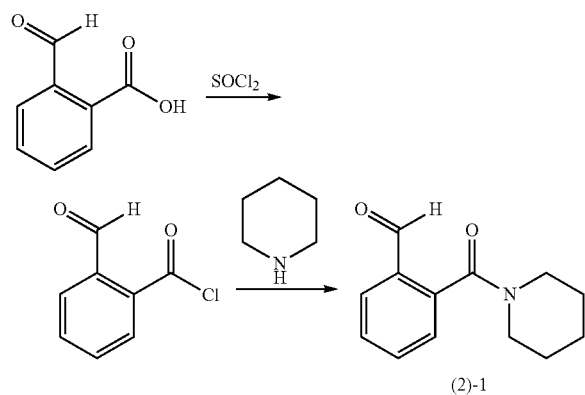

TABLE 2

| | |
|---|---|
| $^1$H-NMR [δ/ppm] (300 MHz, CDCl$_3$) | 1.43 (quint, 2H, J = 6.0 Hz, piperidyl-H) |
| | 1.69 (quint, 3.4H, J = 6.0 Hz, piperidyl-H) |
| | 3.15 (t, 2H, J = 6.0 Hz, piperidyl-H) |
| | 3.80 (t, 2H, J = 6.0 Hz, piperidyl-H) |
| | 7.3-8.0 (m, 4H. Ar—H) |
| | 10.8 (s, 1H, —CHO) |
| $^{13}$C-NMR [δ/ppm] (75 MHz, CDCl$_3$) | 24.3 (sp$^3$ carbon), 25.3 (sp$^3$ carbon) |
| | 26.0 (sp$^3$ carbon), 42.6 (sp$^3$ carbon) |
| | 48.0 (sp$^3$ carbon), 126.8 (sp$^2$ carbon) |
| | 129.1 (sp$^2$ carbon), 130.0 (sp$^2$ carbon) |
| | 132.5 (sp$^2$ carbon), 134.1 (sp$^2$ carbon) |
| | 139.0 (sp$^2$ carbon), 167.6 (C=O carbon) |
| | 190.5 (C=O, carbon) |
| ESI-Positive-HR [M + Na]$^+$ | Calculated value: 240.10005 |
| | Measured value: 240.10015 |

The obtained compound (2)-1 was subjected to simultaneous measurement of Thermogravimetry-Differential Thermal Analysis (TG-DTA) under the conditions of a heating rate of 5° C./min and a measurement temperature range of 20° C. to 500° C., and it was confirmed that this compound decomposed at 240.2° C.

Test Example 1

(Confirmation of behavior of compound (1)-1 in solvent under light irradiation) The above-obtained compound (1)-1 was dissolved in acetonitrile so as to have a concentration of 2.0×10$^{-5}$ mol/L. Then, using a low pressure mercury lamp, the illuminance was set to 1.2 mW/cm$^2$, the exposure dose was set to 0, 60, 240, 600 or 960 mJ/cm$^2$, and the obtained acetonitrile solution was irradiated with light having a wavelength of 254 nm. Then, the absorbance of the compound (1)-1 was measured. The results are shown in FIG. 1.

In Test Example 1, the molar absorption coefficient was £254=1.6×10$^4$ L/(mol cm). As is clear from FIG. 1, as compared with the spectrum in the case of the exposure doses of 0 mJ/cm$^2$, that is, the spectrum in the case of no light irradiation, in the spectrum for other doses, both increasing peak and decreasing peak exist, and from this measurement result, it was confirmed that a base was generated from the compound (1)-1 by light irradiation.

Test Example 2

(Confirmation of behavior of compound (1)-1 in polymer solid under light irradiation) Polytetramethylene glycol (0.20 g), compound (1)-1 (0.017 g, 8.5% by mass with respect to polytetramethylene glycol), and chloroform (1.2 g) were blended and stirred at 25° C. for 1 minute to obtain a resin composition for the test.

Figure 2:
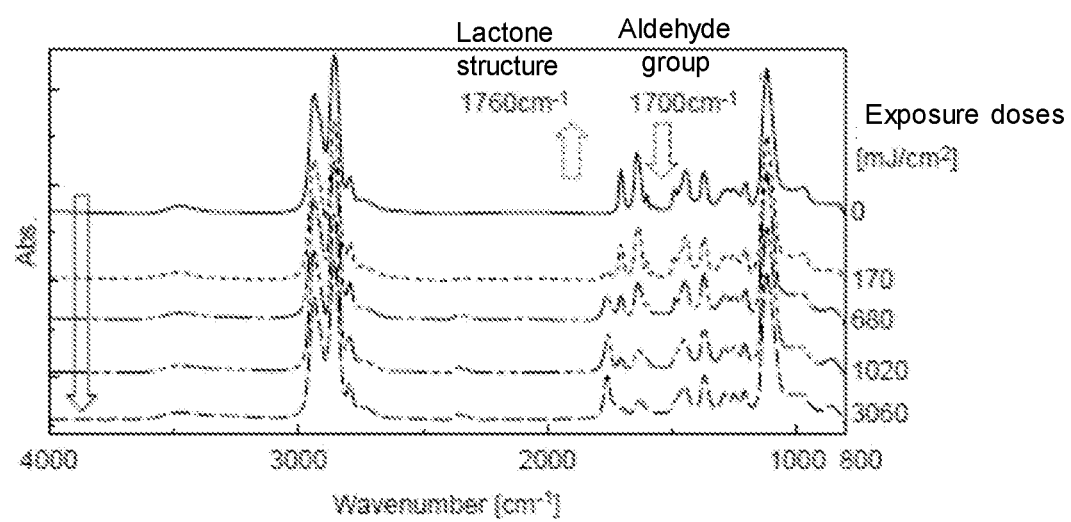
FIG. 2 is a data that illustrates the measurement result of IR spectra of the compound (1)-1 in Test Example 2.
Figure 3:
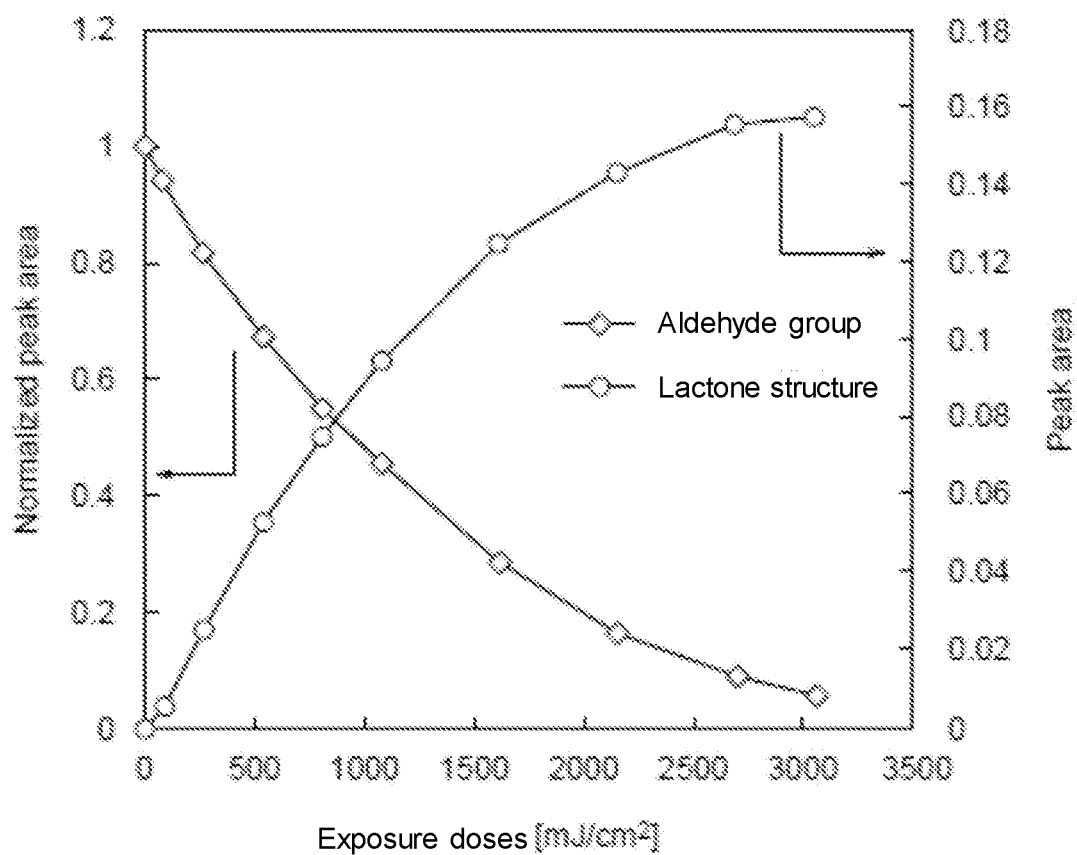
FIG. 3 is a graph illustrating the relationship between the exposure doses in the compound (1)-1 and the peak areas of an aldehyde group and a lactone structure in IR spectra in Test Example 2.

Next, the resin composition for the test was applied onto a calcium fluoride plate by a spin coating method under the conditions of 3000 rpm and 30 seconds, the thus-obtained coating film was heated at 60° C. for 3 minites, and then using a low pressure mercury lamp, the illuminance was set to 1.8 mW/cm$^2$, and the coating film was irradiated with light having a wavelength of 254 nm. At this time, the peak intensity (1700 cm$^-$) derived from the C=O expansion and contraction vibration of the aldehyde group and the peak intensity (1760 cm$^{-1}$) derived from the C=O expansion and contraction vibration of the lactone structure were measured with a Fourier transform infrared spectrophotometer (FT-IR), at specific exposure doses (mJ/cm$^2$) shown in FIG. 2. The result is shown in FIG. 2. FIG. 3 shows a graph illustrating the relationship between the exposure doses in the compound (1) -1 and the peak areas of the aldehyde group and the lactone structure in IR spectra.

As is clear from FIGS. 2 and 3, as the exposure doses increased, the peak intensity derived from the C=O expansion and contraction vibration of the aldehyde group decreased and the peak intensity derived from the C=O expansion and contraction vibration of the lactone structure increased. This is because a compound (1')-1, which is a base, is generated from the compound (1)-1 as shown in the following formula by light irradiation.

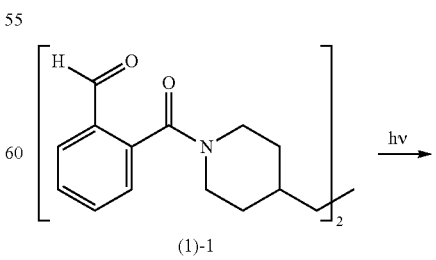

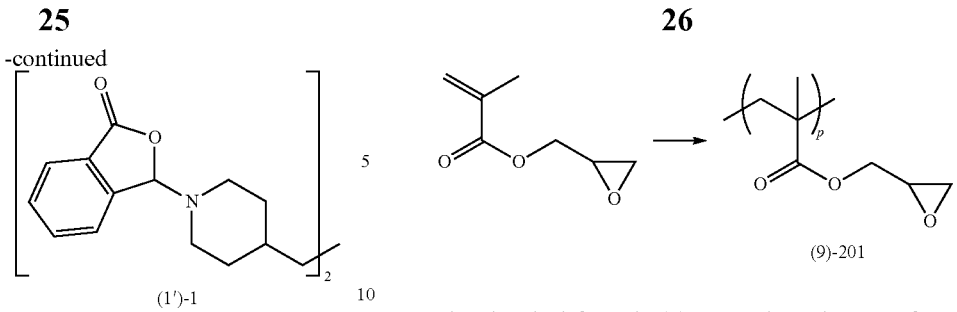

(1')-1

From the aforementioned results, it is assumed that when the compound (2)-1 is irradiated with light, the compound (2')-1, which is a base, is generated from the compound (2)-1 as shown in the following formula.

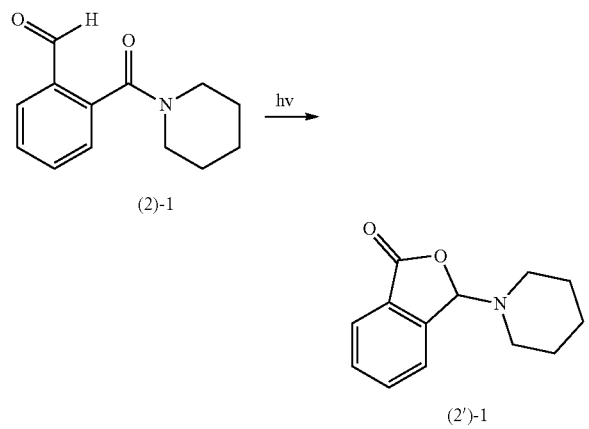

<Production of base-reactive compound (9)-201>

As shown below, a base-reactive compound (9)-201 was produced.

In practice, dried THF (45 mL) was added to glycidyl methacrylate (6.13 g, 43.1 mmol) and the obtained solution was bubbled with nitrogen gas for 30 minutes. Next, the solution after bubbling was heated to 70° C., 2,2'-azobis (isobutyronitrile) (AIBN) (0.074 g, 0.45 mmol) was added thereto, and the thus-obtained mixture was heated to reflux for 8 hours.

Next, the obtained reaction solution was cooled to room temperature, THF was added thereto, and then ethanol, which is a poor solvent, is added to precipitate the objective substance, then this was filtered, and the obtained solid substance was washed with THF to obtain the objective substance.

Further, reprecipitation in which the obtained objective product is dissolved in THF, precipitated by adding ethanol, taken out by filtration, and washed with THF was repeated twice.

From the above, the objective base-reactive compound (9)-201 was obtained as a white solid (yield 4.37 g, yield 71%).

Regarding the obtained compound (9)-201, the analysis result of $^1$H-NMR is shown in Table 3.

The weight average molecular weight (Mw) in terms of standard polystyrene of the base-reactive compound (9)-201 determined by gel permeation chromatography (GPC) was 27454, and the molecular weight dispersion (Mw/Mn) was 1.52.

In the chemical formula (9)-201, p is an integer of 2 or more.

TABLE 3

| $^1$H-NMR [δ/ppm] (500 MHz, CDCl$_3$) | 1.0-1.1 (br, 3H, —CH$_3$) |
|---|---|
| | 1.9-2.0 (br, 2H, —CH$_2$—C—) |
| | 2.64 (br, 1H, —OCH$_2$—) |
| | 2.85 (br, 1H, —OCH$_2$—) |
| | 3.24 (br, 1H, —CH$_2$CHO—) |
| | 3.82 (br, 1H, —OCOCH$_2$—) |
| | 4.31 (br, 1H, —OCOCH$_2$—) |

Example 1

(Production of Photoreactive Composition)

The base-reactive compound (9)-201 (0.14 g), the compound (1)-1 (0.034 g, 5 mol % with respect to glycidyl methacrylate, which is a raw material of the base-reactive compound) and acetonitrile (0.68 g, about 5.0 times by mass of the base-reactive compound) were blended and stirred at 25° C. for 1 minute to obtain a photoreactive composition.

(Production of Reaction Product)

Figure 4:
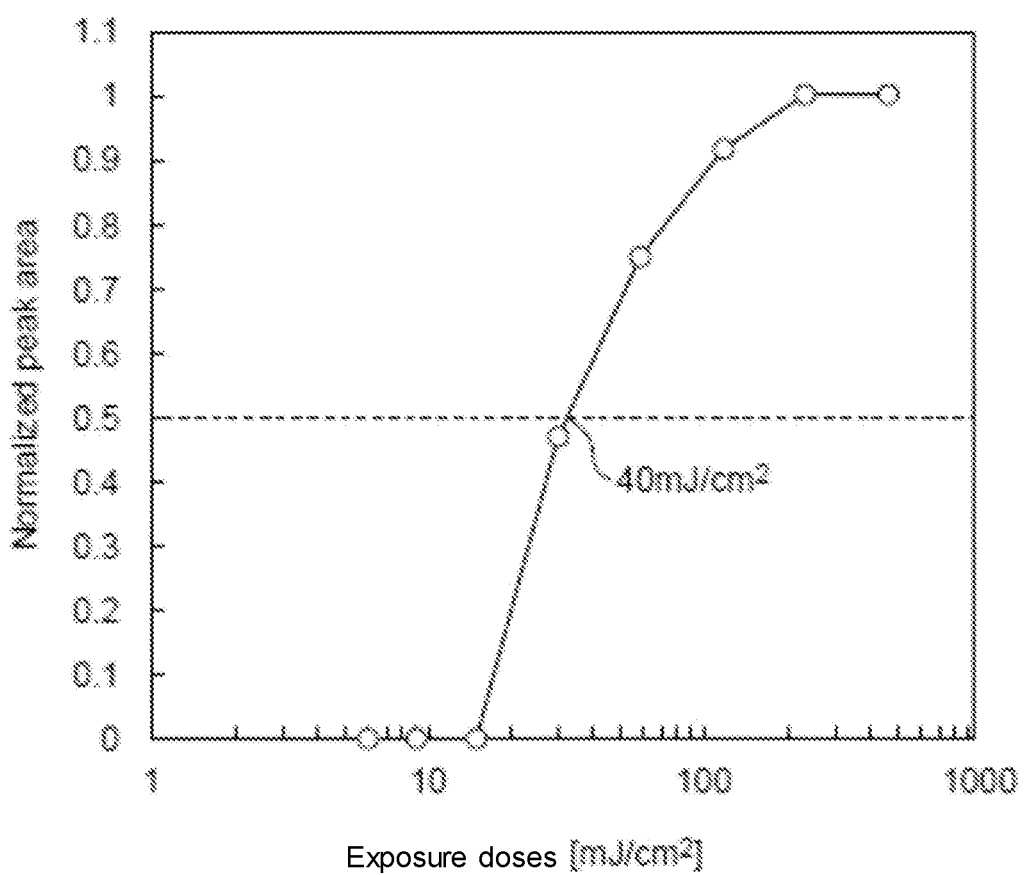
FIG. 4 is a graph illustrating the relationship between the exposure doses and normalized film thicknesses of coating films in Example 1.

The photoreactive composition obtained above was applied onto a silicon wafer by a spin coating method under the conditions of 2000 rpm and 30 seconds, and the thickness of the obtained coating film (thickness of the coating film before light irradiation) was measured. Next, this coating film (photoreactive composition layer) was heated (pre-baked) at 60° C. for 3 minute, and then using a low pressure mercury lamp, the illuminance was set to 1.2 mW/cm$^2$, and the coating film was irradiated with light having a wavelength of 254 nm. Nine types of coating films in which exposure doses were adjusted to 0 to 480 mJ/cm$^2$ as shown in FIG. 4 were prepared and heated (post-baked) at 100° C. for 90 minutes. From the above, regarding the coating films with exposure doses other than 0 mJ/cm$^2$, it was attempted to finally make the coating films into reaction products by polymerizing the base-reactive compound (9)-201.

Next, after washing these post-baked coating films with chloroform, the thicknesses of eight types of the coating films after the washing (thicknesses of the post-baked coating films) were measured, and the normalized film thicknesses of the eight types of the coating films were calculated by the following formula (ii). The results are shown in FIG. 4.

[Normalized film thickness]=[Thickness of coating film after post-baking]/[Thickness of coating film before light irradiation]    (ii)

Example 2

In the production of a photoreactive composition, the photoreactive composition was obtained in the same manner as in Example 1 except that the compound (1)-1 (0.017 g, 2.5 mol % with respect to glycidyl methacrylate, which is a raw material of the base-reactive compound), and acetonitrile (0.70 g, about 5.0 times by mass of the base-reactive compound) were blended.

Next, the normalized film thicknesses of the coating films were calculated under the same conditions as in Example 1. The results are shown in FIG. 5.

Comparative Example 1

A photoreactive composition was obtained in the same manner as in Example 1 except that the compound (2)-1 (5 mol % with respect to glycidyl methacrylate, which is a raw material of the base-reactive compound) was used instead of the compound (1)-1.

Figure 5:
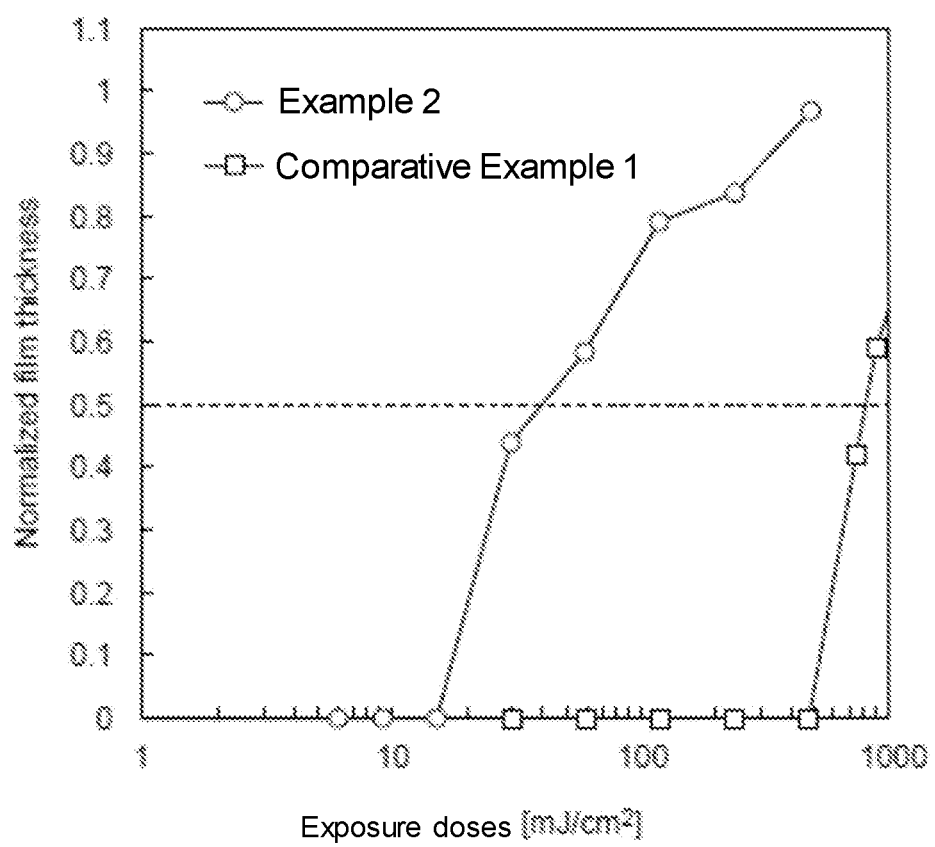
FIG. 5 is a graph illustrating the relationship between the exposure doses and residual normalized film thicknesses of coating films in Example 2 and Comparative Example 1.

Next, the normalized film thicknesses of the coating films were calculated under the same conditions as in Example 1 except that the illuminance was set to 1.2 mW/cm$^2$, and exposure doses were adjusted to 0 to 1000 mJ/cm$^2$ shown in FIG. 5. The results are shown in FIG. 5.

As shown in FIG. 5, in Example 2, the normalized film thicknesses were higher when the exposure doses were the same as in Comparative Example 1. This is because the compound (1')-1, which is the base generated from the compound (1)-1 in Example 2, functions more preferably as a catalyst than the compound (2')-1, which is the base generated from the compound (2)-1 in Comparative Example 1, the reactivity of the base-reactive compound (9)-201 is high, and the production efficiency of the reaction product is high.

Further, from the graph of FIG. 5, it can be read that the exposure doses at which the normalized film thickness is 0.5 (50%) in Example 2 is about 44 mJ/cm$^2$, and the exposure doses at which the normalized film thickness is 0.5 (50%) in Comparative Example 1 is about 790 mJ/cm$^2$. From this, it can be seen that in Example 2, the reaction product can be suitably produced with smaller exposure doses.

Example 3

(Production of Photoreactive Composition)

The base-reactive compound (9)-201 (0.14 g), the compound (1)-1 (0.017 g, 2.5 mol % with respect to glycidyl methacrylate, which is a raw material of the base-reactive compound), t-butylanthracene (0.090 g, 10 mol % with respect to the compound (1)-1), which is a sensitizer and cyclopentanone (0.70 g, about 5.0 times by mass of the base-reactive compound) were blended and stirred at 25° C. for 1 minute to obtain a photoreactive composition.

(Production of Reaction Product)

The photoreactive composition obtained above was applied onto a silicon wafer by a spin coating method under the conditions of 1500 rpm and 20 seconds, and the thickness of the obtained coating film (thickness of the coating film before light irradiation) was measured. Next, this coating film (photoreactive composition layer) was heated (pre-baked) at 60° C. for 1 minute, and then using an LED lamp, the illuminance was set to 1.2 mW/cm$^2$, and the coating film was irradiated with light having a wavelength of 365 nm. Eight types of coating films in which exposure doses were adjusted to 0 to 1000 mJ/cm$^2$ shown in FIG. 6 were prepared and heated (post-baked) at 100° C. for 90 minutes. From the above, regarding the coating films with exposure doses other than 0 mJ/cm$^2$, it was attempted to finally make the coating films into reaction products by polymerizing the base-reactive compound (9)-201.

The normalized film thicknesses of the coating films were calculated under the same conditions as in Example 1. The results are shown in FIG. 6.

Figure 6:
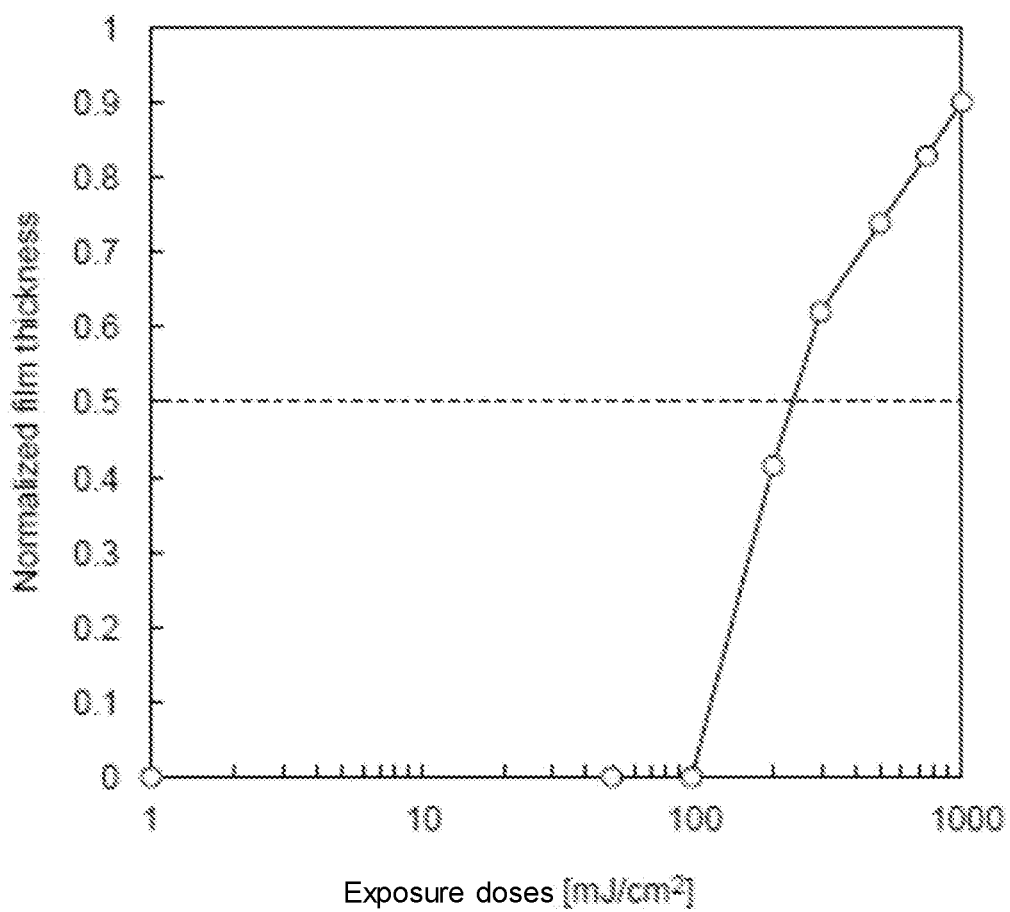
FIG. 6 is a graph illustrating the relationship between the exposure doses and normalized film thicknesses of coating films in Example 3.

As shown in FIG. 6, it was found that the reaction product could be suitably produced at 365 nm, which is a long wavelength ultraviolet region of 300 nm or more, by using the sensitizer.

Example 4

(Production of Photoreactive Composition)

A base-reactive compound (9)-301 (0.24 g) as shown below, the compound (1)-1 (0.041 g, 10 mol % with respect to the methoxy group in the base-reactive compound) and cyclopentanone (1.1 g) were blended and stirred at 25° C. for 1 minute to obtain a photoreactive composition.

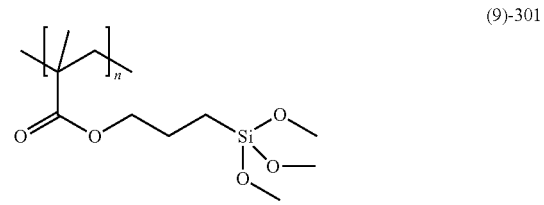

(9)-301

(Production of Reaction Product)

The photoreactive composition obtained above was applied onto a silicon wafer by a spin coating method under the conditions of 1500 rpm and 20 seconds, and the thickness of the obtained coating film (thickness of the coating film before light irradiation) was measured. Next, this coating film (photoreactive composition layer) was heated (pre-baked) at 60° C. for 1 minute, and then using a low pressure mercury lamp, the illuminance was set to 1.2 mW/cm$^2$, and the coating film was irradiated with light having a wavelength of 254 nm. Three types of coating films in which exposure doses were adjusted to 1000 mJ/cm$^2$ were prepared and heated (post-baked) at 60° C., 80° C. or 100° C. for 30 minutes, respectively. From the above, it was attempted to finally make the three types of coating films into reaction products by polymerizing the base-reactive compound (9)-301.

In Example 4, regarding the coating film before light irradiation, the coating film after light irradiation, the coating film heated for another 20 minutes after light irradiation, and the coating film heated for another 60 minutes after light irradiation, the peak intensity (2830 cm$^{-1}$) derived from the C—H expansion and contraction vibration of the methoxy group was measured with a Fourier transform infrared spectrophotometer (FT-IR). The results are shown in FIG. 7.

Figure 8:
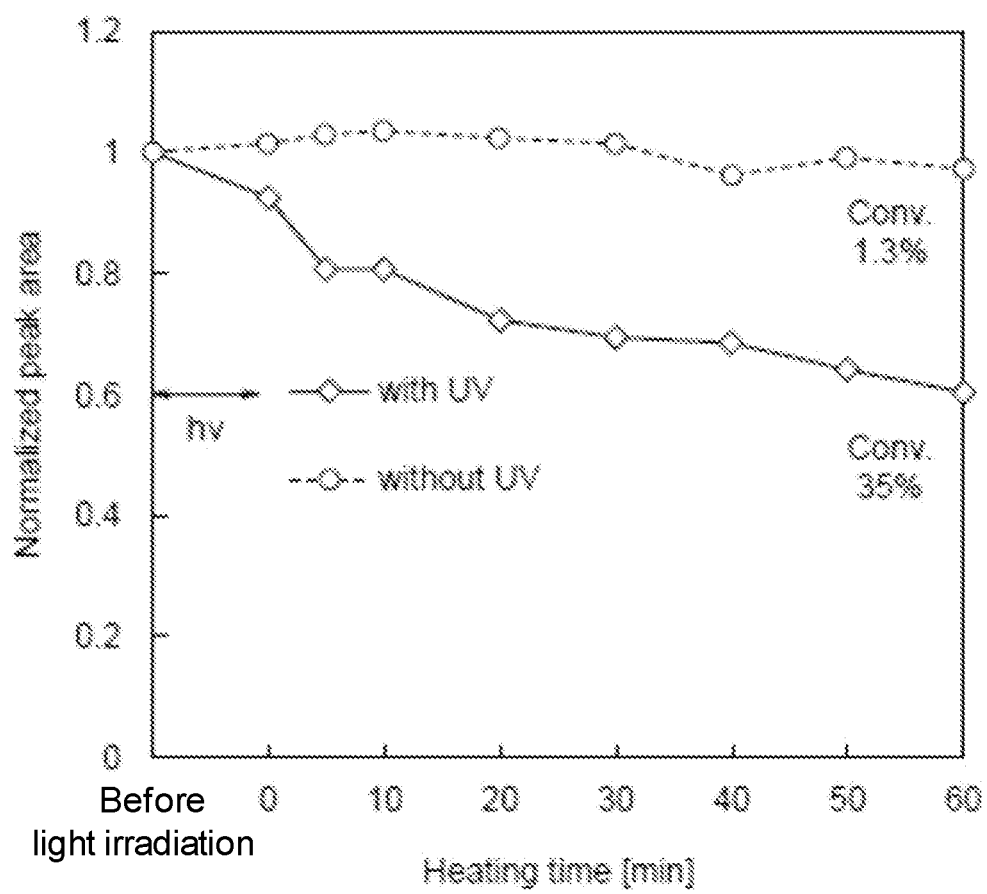
FIG. 8 is a graph illustrating the relationship between the heating time and the peak areas derived from a methoxy group under the light irradiation condition and the light non-irradiation condition in Example 4.
Figure 9:
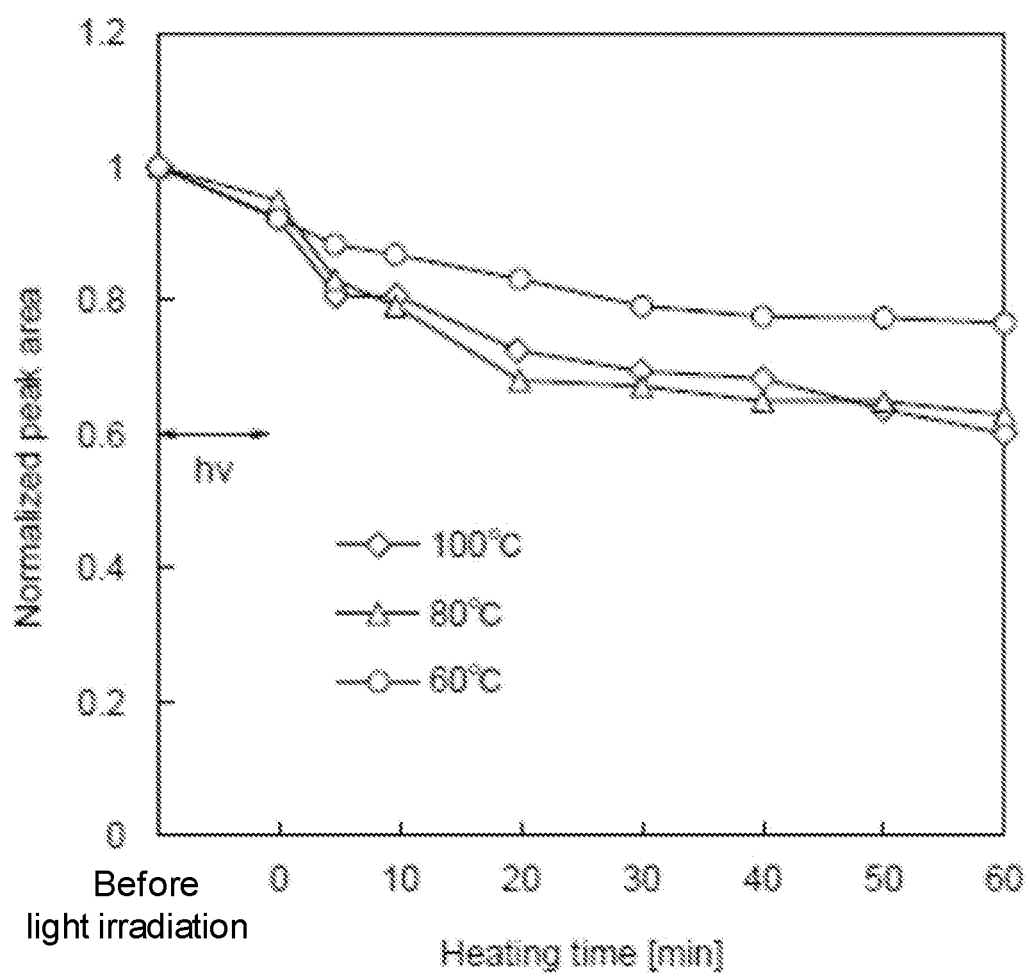
FIG. 9 is a graph illustrating the relationship between the heating time and the peak areas derived from a methoxy group under the light irradiation condition in Example 4.

Further, when the coating films before light irradiation were heated at 100° C. for 0 to 60 minutes, and when the coating films before light irradiation were irradiated with light under the conditions of the illuminance 1.2 mW/cm$^2$, exposure doses 1000 mJ/cm$^2$ and wavelength 254 nm, and then heated at 100° C. for 0 to 60 minutes, the relationship between the heating time and the peak area of the methoxy group is shown in FIG. 8. Further, when the coating films before light irradiation were irradiated with light under the conditions of the illuminance 1.2 mW/cm$^2$, exposure doses 1000 mJ/cm$^2$ and wavelength 254 nm, and then heated at 60° C., 80° C. or 100° C. for 0 to 60 minutes, the relationship between the heating time and the peak area of the methoxy group is shown in FIG. 9.

Further, the pencil hardness of the cured product obtained by heating the coating film before light irradiation at 60° C., 80° C. or 100° C. for 60 minutes and the cured product obtained by irradiating the coating film before light irradiation with light under the aforementioned conditions, and then heating it at 60° C., 80° C. or 100° C. for 60 minutes was determined. The results are shown in FIG. 10.

Figure 7:
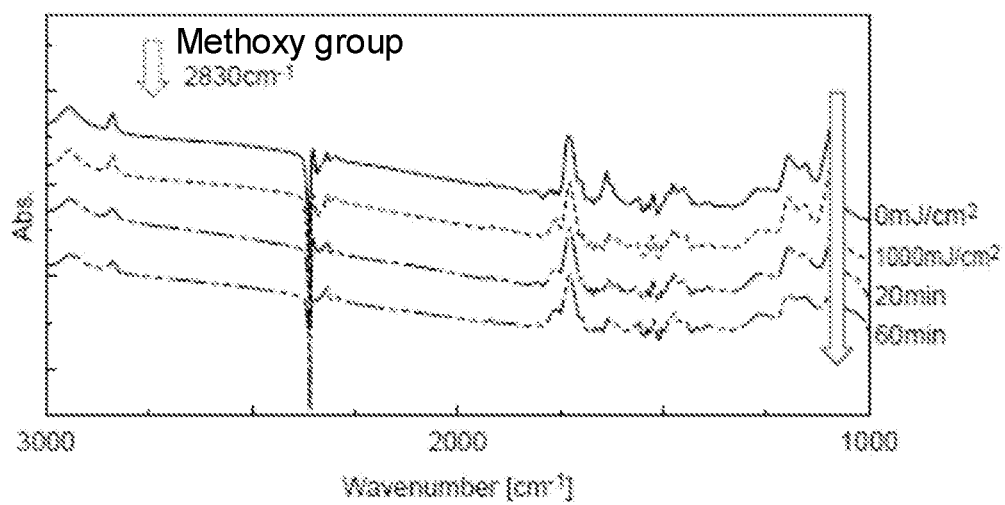
FIG. 7 is a data that illustrates the measurement result of IR spectra of the compound (9)-301 in Example 4.

From FIG. 7, it was confirmed that the methoxy group in the coating film was reduced by irradiating the coating film with light and heating it. Further, from FIGS. 8 and 9, it was confirmed that the reduction rate of the methoxy group differed depending on the presence or absence of light irradiation on the coating film and the degree of heating the coating film.

Figure 10:
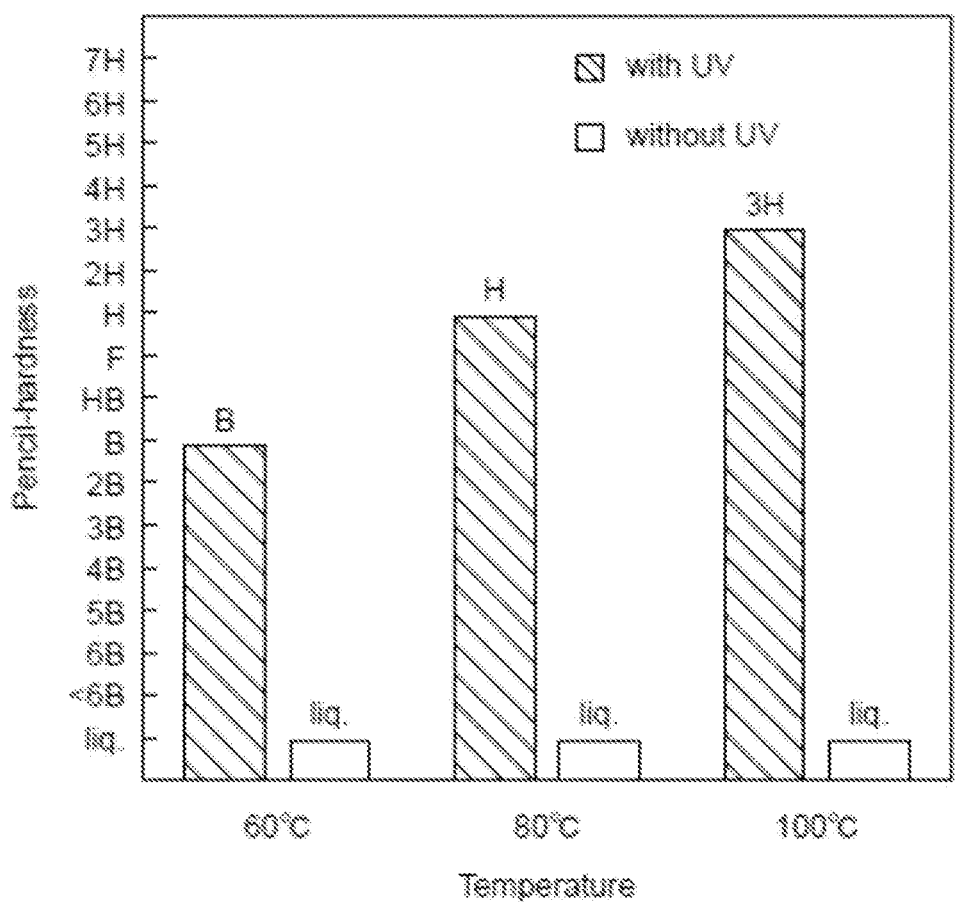
FIG. 10 is a graph illustrating the relationship between the heating temperature and the pencil hardness of the obtained cured products in Example 4.

From FIG. 10, it was confirmed that the cured product excellent in pencil hardness was obtained as a reaction product by irradiating the coating film with light and heating it.

The disclosure of Japanese Patent Application No. 2019-164869 filed on Sep. 10, 2019 is herein incorporated by reference in its entity.

All documents, patent applications, and technical standards described herein are herein incorporated by reference, as if each individual document, patent application, and technical standard were specifically and individually indicated to be incorporated by reference.

The invention claimed is:

1. A photobase generator, comprising a compound including:
    first skeletons represented by the following formula (a); and
    a second skeleton including nitrogen atoms bonding to bonding positions of the first skeletons to form amide groups,
    wherein, in a molecule, a number of the first skeletons is two or more, a number of the nitrogen atoms, configuring the amide groups, in the second skeleton is the same as the number of the first skeletons, and at least one of the nitrogen atoms configuring the amide groups is converted into a nitrogen atom configuring a secondary amine or a tertiary amine by light irradiation:

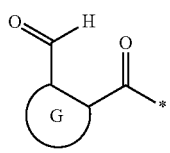

(a)

wherein, in formula (a), G is a divalent aromatic group, and * represents the bonding position with the nitrogen atom.

2. The photobase generator according to claim 1, wherein the second skeleton is a structure represented by the following formula (b):

(b)

wherein, in formula (b), each $R_y$ independently represents a hydrogen atom or a hydrocarbon group that may have a substituent; * represents a bonding position that forms a single bond by bonding with * in formula (a); ** represents a bonding position bonded to $R_x$, which is an n-valent linking group, or a bonding position to a linear chain or a side chain of a high molecular compound; n represents an integer of 2 or more, and is a same value as the number of the first skeletons; each $R_y$ may be independently bonded to $R_x$ or the linear chain or the side chain of the high molecular compound to form a ring structure; and the n first skeletons bonded to * in the formula (b) may be the same or different.

3. The photobase generator according to claim 1, wherein the number of the first skeletons is two, and the second skeleton is a structure represented by the following formula (b-1):

(b-1)

wherein, in formula (b-1), each of $R_5$ and $R_6$ independently represents a hydrogen atom or a hydrocarbon group that may have a substituent; $R_7$ represents a divalent linking group; represents a bonding position that forms a single bond by bonding with * in formula (a); two or more of $R_5$ to $R_7$ may be independently bonded to each other to form a ring structure; and the two first skeletons bonded to * in the formula (b-1) may be the same or different.

4. A photoreactive composition, comprising:
the photobase generator according to claim 1; and
a base-reactive compound,
wherein the base-reactive compound includes a functional group that is converted, by the action of a base, into a group exhibiting reactivity, or includes a group that reacts in response to the action of a base.

5. A photoreactive composition, comprising:
the photobase generator according to claim 2; and
a base-reactive compound,
wherein the base-reactive compound includes a functional group that is converted, by the action of a base, into a group exhibiting reactivity, or includes a group that reacts in response to the action of a base.

6. A photoreactive composition, comprising:
the photobase generator according to claim 3; and
a base-reactive compound,
wherein the base-reactive compound includes a functional group that is converted, by the action of a base, into a group exhibiting reactivity, or includes a group that reacts in response to the action of a base.

* * * * *